United States Patent
Gilly et al.

(10) Patent No.: US 11,274,336 B2
(45) Date of Patent: *Mar. 15, 2022

(54) METHOD OF CALIBRATING A NUCLEIC ACID ANALYZER

(71) Applicant: Gen-Probe Incorporated, San Diego, CA (US)

(72) Inventors: Michael J. Gilly, San Diego, CA (US); Sangeetha Vijaysri Nair, San Diego, CA (US); James M. Carrick, Lanham, MD (US); Xianqun Wang, San Marcos, CA (US); Susan K. Yamagata, Encinitas, CA (US)

(73) Assignee: Gen-Probe Incorporated, San Diego, CA (US)

(*) Notice: Subject to any disclaimer, the term of this patent is extended or adjusted under 35 U.S.C. 154(b) by 935 days.

This patent is subject to a terminal disclaimer.

(21) Appl. No.: 15/912,962

(22) Filed: Mar. 6, 2018

(65) Prior Publication Data

US 2018/0346976 A1    Dec. 6, 2018

Related U.S. Application Data

(63) Continuation of application No. 13/952,338, filed on Jul. 26, 2013, now Pat. No. 9,932,628.

(60) Provisional application No. 61/792,140, filed on Mar. 15, 2013, provisional application No. 61/676,821, filed on Jul. 27, 2012.

(51) Int. Cl.
*C12Q 1/6844* (2018.01)
*G16B 40/00* (2019.01)
*C12Q 1/6851* (2018.01)

(52) U.S. Cl.
CPC ........ *C12Q 1/6844* (2013.01); *C12Q 1/6851* (2013.01); *G16B 40/00* (2019.02)

(58) Field of Classification Search
None
See application file for complete search history.

(56) References Cited

U.S. PATENT DOCUMENTS

| | | | |
|---|---|---|---|
| 5,038,852 A | 8/1991 | Johnson et al. | |
| 5,348,889 A | 9/1994 | Terashima et al. | |
| 5,457,027 A | 10/1995 | Nadeau et al. | |
| 5,554,539 A | 9/1996 | Chadney et al. | |
| 5,656,493 A | 8/1997 | Mullis et al. | |
| 5,747,246 A | 5/1998 | Pannetier et al. | |
| 5,766,889 A | 6/1998 | Atwood | |
| 5,789,153 A | 8/1998 | Falkner et al. | |
| 5,834,255 A | 11/1998 | van Gemen et al. | |
| 5,837,501 A | 11/1998 | Beumer et al. | |
| 5,840,487 A | 11/1998 | Nadeau et al. | |
| 5,858,658 A | 1/1999 | Haemmerle et al. | |
| 5,952,202 A | 9/1999 | Aoyagi et al. | |
| 6,066,458 A | 5/2000 | Haaland et al. | |
| 6,277,584 B1 | 8/2001 | Chu et al. | |
| 6,387,621 B1 | 5/2002 | Wittwer | |
| 6,534,645 B2 | 3/2003 | McMillan | |
| 6,713,297 B2 | 3/2004 | McMillan et al. | |
| 6,783,934 B1 | 8/2004 | McMillan et al. | |
| 6,814,934 B1 | 11/2004 | Higuchi | |
| 6,818,437 B1 | 11/2004 | Gambini et al. | |
| 6,911,327 B2 | 6/2005 | McMillan et al. | |
| 7,125,691 B2 | 10/2006 | Sagner et al. | |
| 7,228,237 B2 | 6/2007 | Woo et al. | |
| 7,348,164 B2 | 3/2008 | Andrus et al. | |
| 7,680,603 B2 | 3/2010 | Kurnik | |
| 7,680,604 B2 | 3/2010 | Kurnik | |
| 7,739,054 B2 | 6/2010 | Carrick et al. | |
| 7,788,039 B2 | 8/2010 | Vess | |
| 7,831,417 B2 | 11/2010 | Carrick et al. | |
| 7,930,106 B2 | 4/2011 | Carrick | |
| 9,932,628 B2 * | 4/2018 | Gilly ............... | C12Q 1/6844 |
| 2002/0031768 A1 | 3/2002 | McMillan et al. | |
| 2003/0165832 A1 | 9/2003 | Sagner et al. | |
| 2004/0096819 A1 | 5/2004 | McMillan et al. | |
| 2005/0118620 A1 | 6/2005 | Vess | |
| 2005/0255516 A1 | 11/2005 | McMillan et al. | |
| 2006/0008809 A1 | 1/2006 | Li et al. | |
| 2006/0204972 A1 | 9/2006 | Kurnik | |
| 2006/0224330 A1 | 10/2006 | Kurnik | |
| 2006/0292571 A1 | 12/2006 | Babiel et al. | |
| 2007/0143070 A1 | 6/2007 | Kurnik et al. | |
| 2008/0133198 A1 | 6/2008 | Carrick | |
| 2008/0182260 A1 | 7/2008 | Timmermans et al. | |

(Continued)

FOREIGN PATENT DOCUMENTS

DE    19614852 A1    10/1997
EP    0422646 A2    4/1991

(Continued)

OTHER PUBLICATIONS

Gill et al. Nucleid Acid Isothermal Amplification Technologies-A Review Nucleosides, Nucleotides, and Nucleic Acids vol. 27, pp. 224-243 (2008).

(Continued)

*Primary Examiner* — John S Brusca

(74) *Attorney, Agent, or Firm* — McNeill Baur PLLC

(57) ABSTRACT

Method and system for quantifying target nucleic acids using real-time amplification and internal calibration adjustment. The invention employs dual reference calibration curves for approximating a complete calibration curve from only a single adjustment calibrator amplified on the instrument that is to be calibrated.

20 Claims, 8 Drawing Sheets

(56) References Cited

U.S. PATENT DOCUMENTS

| | | |
|---|---|---|
| 2009/0136951 A1 | 5/2009 | Hart et al. |
| 2010/0041040 A1 | 2/2010 | Babiel et al. |
| 2011/0147610 A1 | 6/2011 | Macioszek et al. |
| 2014/0030720 A1 | 1/2014 | Gilly et al. |

FOREIGN PATENT DOCUMENTS

| | | |
|---|---|---|
| EP | 0525882 A1 | 2/1993 |
| EP | 0623682 A1 | 11/1994 |
| EP | 0640828 A1 | 3/1995 |
| EP | 0872562 A1 | 10/1998 |
| EP | 1041158 A2 | 10/2000 |
| EP | 1138784 A2 | 10/2001 |
| EP | 1518935 A1 | 3/2005 |
| EP | 1701275 A2 | 9/2006 |
| EP | 1798542 A1 | 6/2007 |
| EP | 1798652 A1 | 6/2007 |
| EP | 1804172 A2 | 7/2007 |
| EP | 1842925 A1 | 10/2007 |
| WO | WO 1997/012058 A1 | 9/1997 |
| WO | WO 1997/046714 A1 | 12/1997 |
| WO | WO 1998/058079 A1 | 12/1998 |
| WO | WO 2001/066799 A2 | 9/2001 |
| WO | WO 2005/062040 A2 | 7/2005 |

OTHER PUBLICATIONS

PCT International Preliminary Report on Patentability, International Application No. PCT/US2013/052323, dated Jan. 27, 2015.

PCT Written Opinion & International Search Report, International Application No. PCT/US2013/052323, dated May 2, 2014.

Thell in et al. A decade of improvements in quantification of gene expression and internal standard selection Biotechnology Advances vol. 27, pp. 323-333 (2009).

Wong et al. Real-time PCR for mRNA quantitation Bio Techniques vol. 39, pp. 75-85 (2005).

* cited by examiner

METHOD OF CALIBRATING A NUCLEIC ACID ANALYZER

RELATED APPLICATIONS

This application is a continuation of U.S. application Ser. No. 13/952,338, filed Jul. 26, 2013, which claims the benefit of U.S. Provisional Application No. 61/676,821, filed Jul. 27, 2012; and U.S. Provisional Application No. 61/792,140, filed Mar. 15, 2013. The entire disclosures of these earlier applications are hereby incorporated by reference.

FIELD OF THE INVENTION

The present invention relates to the field of biotechnology. More specifically, the invention relates to calibration methods and systems for quantifying polynucleotides using results from real-time amplification procedures.

BACKGROUND OF THE INVENTION

Methods involving the kinetic analysis of in vitro nucleic acid amplification are now routinely used for quantifying analyte nucleic acids. In these procedures, sometimes referred to as "real-time" amplification procedures, the amount of amplicon present in a nucleic acid amplification reaction mixture is monitored as a function of time over the course of the amplification procedure. Fully automated real-time nucleic acid assays require machine executable algorithms capable of analyzing the time-dependent data acquired during the reaction. In this regard, there is a requirement for data processing algorithms that accurately output an amount or concentration of a nucleic acid that would give rise to an observed amplification result.

Difficulties associated with quantifying the absolute amount of a specific nucleic acid target have been appreciated in the patent literature. These difficulties have been attributed to the exponential nature of the amplification process, and the fact that small differences in any of the variables that control reaction rates, including the length and nucleotide sequence of the primer pairs, can lead to dramatic differences in amplicon yield. Wang et al., in U.S. Pat. No. 5,219,727 described the use of an internal standard that amplified using the same primers that amplified the analyte polynucleotide, and addressed the fact that use of an unrelated cDNA as a standard necessitated a second set of oligonucleotide primers unrelated to the specific target nucleic acid being quantified. According to Wang et al., analyses which use two sets of unrelated primers can only provide a relative comparison of two independent amplification reactions rather than an absolute measure of a target nucleic acid concentration. Others have followed this teaching and employed internal standards that resemble the target of interest by having similar sequences, and by amplifying with a common pair of primers (see published U.S. patent application Ser. No. 10/230,489). Still others have described quantitative methods that rely on determining the efficiency of amplification (see published European Patent Application EP 1138784). Methods involving determination of amplification ratios for control and target sequences also have been described (see U.S. Pat. No. 6,066,458).

The most common methods for performing internal calibration adjustment of real-time nucleic acid amplification results include "within-run" calibration adjustment, and adjustment of a "stored" calibration curve. The first of these methods, illustrated by McMillan et al., in U.S. Pat. No. 6,713,297, requires two or more calibration standards that are conventionally amplified in parallel with analyte nucleic acids in replicates each time a calibration plot is prepared. Unfortunately, this requirement each time an instrument is re-calibrated consumes limited reagents that are generally purchased in kit form, and that may be costly. The second method, illustrated by Carrick in U.S. Pat. No. 7,930,106, advantageously avoids the need to run multiple calibrators each time an instrument is re-calibrated, but still requires preparation of a full calibration plot at some point (e.g., either by a kit manufacturer or end-user). Experience with this technique has shown good ability to reproduce quantitative results using a single calibration standard when the target being quantified is present at high, or very high levels. For example, back-testing confirmed that adjustment of a stored curve using a single adjustment calibrator having $10^7$ target copies advantageously reproduced the full local curve nearly identically in the range of from $10^4$ to $10^8$ target copies. In this case, the adjusted curve deviated from the local curve by no more than 0.6 log copies at an input amount of $10^2$ target copies. Using a single adjustment calibrator having $10^2$ target copies, in contrast, resulted in an adjusted curve deviating by 0.4 log copies at an input target level of $10^3$ target copies, and deviating by 1.6 log copies at an input target level of $10^6$ target copies. Thus, there was a clear benefit to adjusting the stored curve using calibration standards having high target amounts.

Even in view of these useful approaches, there remains a need for automated solutions that permit highly accurate quantitation of nucleic acids using in vitro amplification techniques, where internal calibration adjustment can be executed in a simplified manner. Moreover, it would be desirable to be able to use a single calibration standard that comprises a low concentration of the analyte polynucleotide standard to achieve accurate quantitation across the full dynamic range of target amounts or concentrations to be measured. The present invention addresses these issues.

SUMMARY OF THE INVENTION

Figure 1:
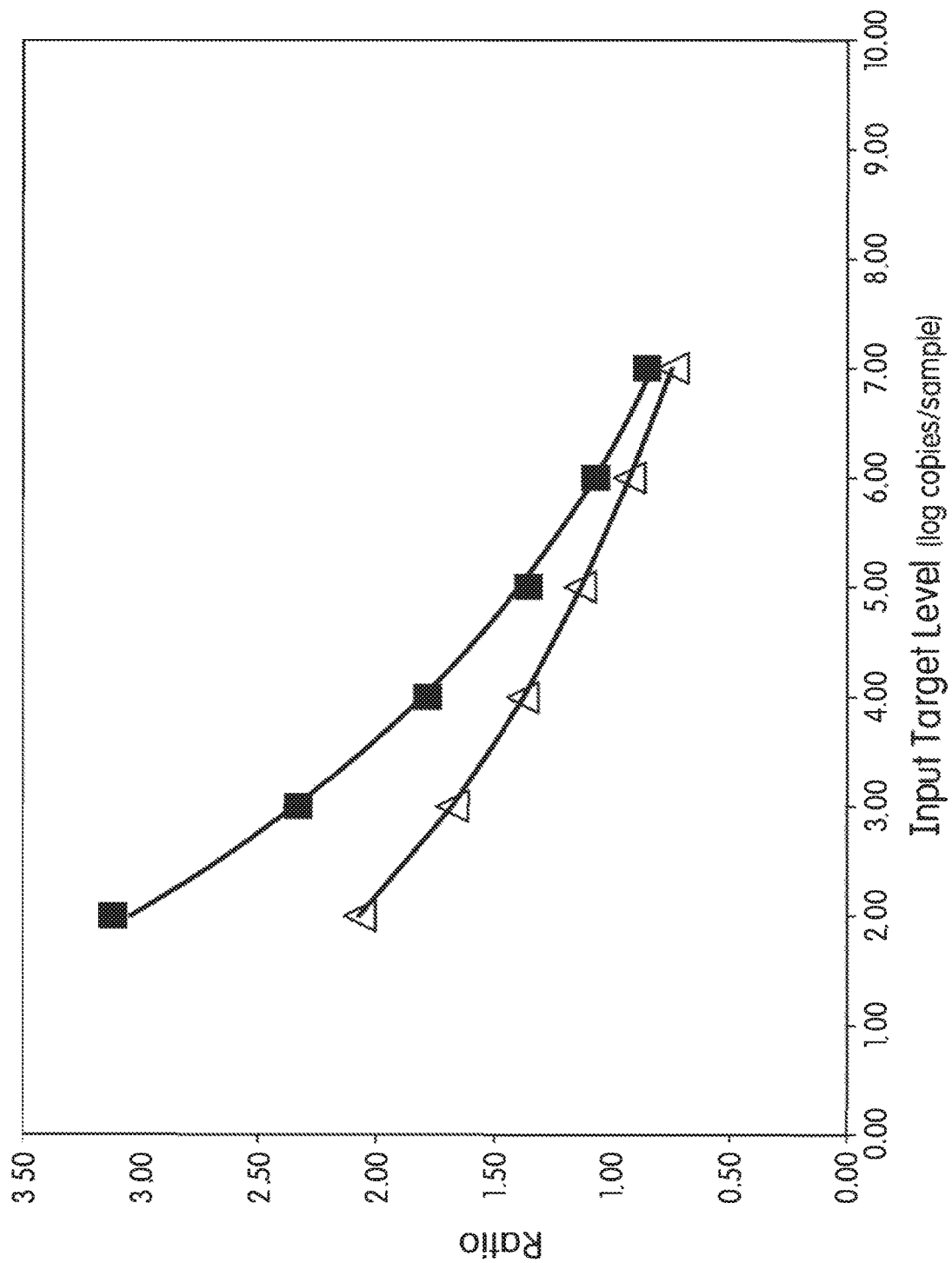
FIG. 1 is a graph showing a master calibration curve (open triangles), and a local calibration curve (filed squares).

A first aspect of the invention relates to a method of establishing an adjusted calibration curve for an assay that quantifies an analyte polynucleotide using a local instrument that amplifies nucleic acids and monitors synthesis of amplification products as amplification is occurring. The method includes the step (a) of obtaining first and second equations respectively defining first and second calibration curves specific for the assay, wherein each of the first and second calibration curves relates normalized indicia of amplification for analyte polynucleotide standards to indicia of amplification for a fixed amount of an internal calibrator polynucleotide that co-amplified therewith as a function of starting amounts of the analyte polynucleotide in amplification reactions of the assay, and wherein each of the calibration curves is different from the other. There also is the step (b) of obtaining an adjustment calibrator including an amount of the analyte polynucleotide and said fixed amount of the internal calibrator polynucleotide. There also is the step (c) of co-amplifying, in a nucleic acid amplification reaction carried out with the local instrument, the analyte polynucleotide and the internal calibrator polynucleotide of the adjustment calibrator. There also is the step (d) of determining indicia of amplification for each of the analyte polynucleotide and the internal calibrator polynucleotide of the adjustment calibrator that co-amplified in the nucleic acid amplification reaction. There also is the step (e) of normalizing the determined indicia of amplification for the analyte polynucleotide to the determined indicia of amplification for the internal calibrator polynucleotide of the adjustment calibrator. There also is the step (f) of determining a relative relationship between the difference between the normalized value determined for the adjustment calibrator and one of the first and second calibration curves at the amount of the analyte polynucleotide of the adjustment calibrator and, the difference between the first and second calibration curves at the amount of the analyte polynucleotide of the adjustment calibrator. There also is the step (g) of establishing a calibration plot that maintains said relative relationship to the first and second calibration curves at all values of analyte polynucleotide standard, thereby establishing the adjusted calibration curve for the assay on the local instrument. In accordance with a first generally preferred embodiment, step (a) and step (b) collectively include obtaining a kit including the adjustment calibrator and tangible embodiments of the first and second equations. When this is the case, the tangible embodiments of the first and second equations include a machine-readable barcode. In accordance with a second generally preferred embodiment, the nucleic acid amplification reaction of step (c) includes an isothermal nucleic acid amplification reaction. In accordance with a third generally preferred embodiment, step (g) includes establishing the calibration plot with an electronic spreadsheet. In accordance with a fourth generally preferred embodiment, there is the further step of quantifying the analyte polynucleotide contained in a test sample by comparing to the calibration plot established in step (g) a normalized indicia of amplification result for the assay performed using the local instrument to amplify and monitor a test reaction that includes the test sample and the fixed amount of the internal calibrator polynucleotide. In accordance with a fifth generally preferred embodiment, amplification reactions used for preparing the first calibration curve and the second calibration curve preferably were not performed with the local instrument. More preferably, step (a) and step (b) collectively include obtaining a kit including the adjustment calibrator and tangible embodiments of the first and second equations. In accordance with a sixth generally preferred embodiment, the first calibration curve, the second calibration curve, and the adjusted calibration curve were prepared using results from amplification reactions performed with three different instruments that amplify nucleic acids and monitor synthesis of amplification products as amplification is occurring. In accordance with a seventh generally preferred embodiment, step (a) includes obtaining tangible embodiments of the first and second equations. In accordance with an eighth generally preferred embodiment, the first and second calibration curves of step (a) are both linear calibration curves. When this is the case, amplification reactions used for preparing the first calibration curve and the second calibration curve were not performed with the local instrument. More preferably, step (a) and step (b) collectively include obtaining a kit including the adjustment calibrator and tangible embodiments of the first and second equations. Further in accordance with the eighth generally preferred embodiment, and wherein the first and second calibration curves of step (a) are both linear calibration curves, there may be the further step of quantifying the analyte polynucleotide contained in a test sample by comparing to the calibration plot established in step (g) a normalized indicia of amplification result for the assay performed using the local instrument to amplify and monitor a test reaction that includes the test sample and the fixed amount of the internal calibrator polynucleotide. More preferably, the first calibration curve, the second calibration curve, and the adjusted calibration curve were prepared using results from amplification reactions performed with three different instruments that amplify nucleic acids and monitor synthesis of amplification products as amplification is occurring. Generally speaking, different preferred embodiments of the invention will concern establishing adjusted linear calibration curves, and adjusted non-linear calibration curves. Thus, in these different situations, the first and second calibration curves, together with the calibration plot established in step (g), can all be linear calibration curves, or can all be non-linear calibration curves.

Another aspect of the invention relates to a method of establishing an adjusted calibration curve for an assay that quantifies an analyte polynucleotide using a local instrument that amplifies nucleic acids and monitors synthesis of amplification products as amplification is occurring. The method includes the step (a) of obtaining an adjustment calibrator including an amount of the analyte polynucleotide and a first amount of an internal calibrator polynucleotide. There also is the step (b) of obtaining, in a machine-readable format, (i) first and second data points from a first calibration curve, each data point from the first calibration curve including a first coordinate for a starting amount of the analyte polynucleotide and a second coordinate for a value for normalized indicia of amplification, and (ii) first and second data points from a second calibration curve, each data point from the second calibration curve including a first coordinate for a starting amount of the analyte polynucleotide and a second coordinate for a value for normalized indicia of amplification, wherein the value of the first coordinate of the first data point from the first calibration curve, the value of the first coordinate of the first data point from the second calibration curve, and the value of the amount of the analyte polynucleotide of the adjustment calibrator are substantially identical to each other, and wherein the value of the first coordinate of the second data point from the first calibration curve, and the value of the first coordinate of the second data point from the second calibration curve are substantially identical to each other. There also is the step (c) of co-amplifying, in a nucleic acid amplification reaction carried out with the local instrument, the analyte polynucleotide and the internal calibrator polynucleotide of the adjustment calibrator. There also is the step (d) of determining indicia of amplification for each of the analyte polynucleotide and the internal calibrator polynucleotide of the adjustment calibrator that co-amplified in the nucleic acid amplification reaction. There also is the step (e) of normalizing the determined indicia of amplification for the analyte polynucleotide to the determined indicia of amplification for the internal calibrator polynucleotide of the adjustment calibrator. There also is the step (f) of determining a relative relationship between (1) the difference between the normalized value determined for the adjustment calibrator in step (e) and the first coordinate of the first data point from the first calibration curve; and (2) the difference between the first coordinates of the first data points from each of the first and second calibration curves. There also is the step (g) of establishing a calibration plot that maintains said relative relationship at all values of analyte polynucleotide standard, thereby establishing the adjusted calibration curve for the assay on the local instrument, wherein the calibration plot includes a data point with a first coordinate that is the value of the starting amount of the analyte polynucleotide of the adjustment calibrator, and a second coordinate that is the normalized value determined for the adjustment calibrator in step (e), and wherein the calibration plot further includes a data point with a first coordinate that is the same as the first coordinates of the second data points from the first and second calibration curves, and a second coordinate that is related to the second coordinates of the second data points from the first and second calibration curves according to the relative relationship determined in step (f). In a first generally preferred embodiment, step (b) includes obtaining first and second equations respectively defining the first and second calibration curves, and further includes calculating, with electronic spreadsheet software, numerical values for the second coordinates for each of the first and second data points from the first and second calibration curves. More preferably, the machine-readable format includes a machine-readable barcode. Alternatively, the machine-readable format includes entries in an electronic spreadsheet of a computer in communication with the local instrument. In accordance with a second generally preferred embodiment, the first calibration curve relates indicia of amplification for the analyte polynucleotide normalized to indicia of amplification for the internal calibrator polynucleotide that co-amplified therewith, in a first plurality of amplification reactions carried out using calibration standards, as a function of starting amounts of the analyte polynucleotide; the second calibration curve relates indicia of amplification for the analyte polynucleotide normalized to indicia of amplification for the internal calibrator polynucleotide that co-amplified therewith, in a second plurality of amplification reactions carried out using calibration standards, as a function of starting amounts of the analyte polynucleotide; each of the first and second plurality of amplification reactions carried out using calibration standards includes a second amount of the internal calibrator polynucleotide; the first amount of the internal calibrator polynucleotide of the adjustment calibrator and the second amount of the internal calibrator polynucleotide are substantially identical; each of the calibration curves is different from the other; and step (g) includes establishing the calibration plot with an electronic spreadsheet. More preferably, the first plurality of amplification reactions and the second plurality of amplification reactions are performed using different instruments that amplify nucleic acids and monitor synthesis of amplification products as amplification is occurring. Still more preferably, the first and second calibration curves of step (b) are both linear calibration curves. Still in accordance with the second generally preferred embodiment, the first plurality of amplification reactions and the second plurality of amplification reactions can be performed using different reaction conditions. Still in accordance with the second generally preferred embodiment, the first plurality of amplification reactions used for preparing the first calibration curve and the second plurality of amplification reactions used for preparing the second calibration curve were not both performed with the local instrument. When this is the case, step (a) and step (b) collectively may include obtaining a kit including the adjustment calibrator and, in the machine-readable format, all of said data points from the first and second calibration curves. Still in accordance with the second generally preferred embodiment, the first calibration curve, the second calibration curve, and the adjusted calibration curve are prepared using results from amplification reactions performed with three different instruments that amplify nucleic acids and monitor synthesis of amplification products as amplification is occurring. Still in accordance with the second generally preferred embodiment, the first and second calibration curves of step (b) are both linear calibration curves. According to a third generally preferred embodiment, step (a) and step (b) collectively include obtaining a kit including the adjustment calibrator and, in the machine-readable format, all of said data points from the first and second calibration curves. According to a fourth generally preferred embodiment, the nucleic acid amplification reaction of step (c) includes an isothermal nucleic acid amplification reaction. According to a fifth generally preferred embodiment, step (g) includes establishing the calibration plot with an electronic spreadsheet. According to a sixth generally preferred embodiment, there is the further step of quantifying the analyte polynucleotide contained in a test sample by comparing to the calibration plot established in step (g) a normalized indicia of amplification result for the assay performed using the local instrument to amplify and monitor a test reaction that includes the test sample and a third amount of the internal calibrator polynucleotide that is substantially identical to the first amount of the internal calibrator polynucleotide of the adjustment calibrator. According to a seventh generally preferred embodiment, the first and second calibration curves of step (b) are both linear calibration curves. When this is the case, amplification reactions used for preparing the first calibration curve and the second calibration curve were not performed with the local instrument. Alternatively, step (a) and step (b) collectively include obtaining a kit including the adjustment calibrator and, in the machine-readable format, all of said data points from the first and second calibration curves. According to yet another alternative, the first calibration curve, the second calibration curve, and the adjusted calibration curve were prepared using results from amplification reactions performed with three different instruments that amplify nucleic acids and monitor synthesis of amplification products as amplification is occurring. Generally speaking, different preferred embodiments of the invention will concern establishing adjusted linear calibration curves, and adjusted non-linear calibration curves. Thus, in these different situations, the first and second calibration curves, together with the calibration plot established in step (g), can all be linear calibration curves, or can all be non-linear calibration curves.

Another aspect of the invention relates to a method of establishing an adjusted calibration curve for quantifying analyte nucleic acids contained in a test sample and amplified with a local instrument that amplifies nucleic acids and monitors synthesis of amplification products as amplification is occurring. The method includes the step (a) of co-amplifying, in a first plurality of real-time amplification reactions, an analyte polynucleotide and an internal calibrator polynucleotide contained in each of a first plurality of calibration standards, wherein each of the first plurality of calibration standards includes different known starting amounts of the analyte polynucleotide and a constant amount of the internal calibrator polynucleotide, whereby indicia of amplification for the analyte polynucleotide and the internal calibrator polynucleotide are determined for each of the first plurality of real-time amplification reactions. There also is the step (b) of co-amplifying, in a second plurality of real-time amplification reactions, the analyte polynucleotide and the internal calibrator polynucleotide contained in each of a second plurality of calibration standards, wherein each of the second plurality of calibration standards includes different known starting amounts of the analyte polynucleotide and said constant amount of the internal calibrator polynucleotide, whereby indicia of amplification for the analyte polynucleotide and the internal calibrator polynucleotide are determined for each of the second plurality of real-time amplification reactions. There also is the step (c) of establishing a first calibration curve that specifies values for indicia of amplification determined for the analyte polynucleotide normalized to indicia of amplification for the internal calibrator polynucleotide that co-amplified therewith in the first plurality of real-time amplification reactions as a function of values of starting amounts of the analyte polynucleotide. There also is the step (d) of establishing a second calibration curve that specifies values for indicia of amplification determined for the analyte polynucleotide normalized to indicia of amplification for the internal calibrator polynucleotide that co-amplified therewith in the second plurality of real-time amplification reactions as a function of values of starting amounts of the analyte polynucleotide. There also is the step (e) of obtaining an adjustment calibrator including a known amount of the analyte polynucleotide and said constant amount of the internal calibrator polynucleotide. There also is the step (f) of co-amplifying, in a real-time amplification reaction performed with the local instrument, the analyte polynucleotide and the internal calibrator polynucleotide of the adjustment calibrator, whereby indicia of amplification for the analyte polynucleotide and the internal calibrator polynucleotide of the adjustment calibrator are determined. There also is the step (g) of normalizing indicia of amplification determined for the analyte polynucleotide to indicia of amplification for the internal calibrator polynucleotide determined for the adjustment calibrator. There also is the step (h) of establishing the adjusted calibration curve by substituting into an equation (1) coordinates of a first point determined by the known amount of the analyte polynucleotide of the adjustment calibrator, and by the normalized indicia of amplification for the analyte polynucleotide determined for the adjustment calibrator, and (2) coordinates of a second point determined by using both of the first and second calibration curves. According to a first generally preferred embodiment, coordinates of the second point in step (h) include coordinates of a point of intersection between the first and second calibration curves. More preferably, the equation of step (h) can be a linear equation. Alternatively, the equation of step (h) can be a non-linear equation. According to a second generally preferred embodiment, coordinates of the second point in step (h) are determined by the value of a predetermined amount of the analyte polynucleotide that is different from the known amount of the analyte polynucleotide of the adjustment calibrator, and by a relative relationship to the first and second calibration curves at the predetermined amount of the analyte polynucleotide; and the relative relationship is established by comparing: (1) the difference between the normalized indicia of amplification for the analyte polynucleotide determined for the adjustment calibrator in step (g) and the first calibration curve at a point where the starting amount of the analyte polynucleotide equals the known amount of the analyte polynucleotide of the adjustment calibrator, and (2) the difference between the first and second calibration curves at the point where the starting amount of the analyte polynucleotide equals the known amount of the analyte polynucleotide of the adjustment calibrator. More preferably, the equation of step (h) can be a linear equation. Alternatively, the equation of step (h) can be a non-linear equation. According to a third generally preferred embodiment, at least one of the first and second plurality of real-time amplification reactions is carried out with an instrument other than the local instrument. According to a fourth generally preferred embodiment, either: the first and second pluralities of real-time amplification reactions are conducted using different real-time instruments; or the first and second pluralities of real-time amplification reactions are conducted using different reaction compositions, and the first calibration curve and the second calibration curve are non-identical. According to a fifth generally preferred embodiment, the first plurality of real-time amplification reactions and the second plurality of real-time amplification reactions are both performed with the local instrument. According to a sixth generally preferred embodiment, the equation of step (h) is a linear equation. According to a seventh generally preferred embodiment, the equation of step (h) is a non-linear equation.

Another aspect of the invention relates to a method of preparing a kit for calibrating a local instrument that amplifies nucleic acid and monitors production of amplification products as amplification is occurring. The method includes the step (a) of co-amplifying, in a first plurality of real-time nucleic acid amplification reactions, the analyte polynucleotide and the internal calibrator contained in each of a first plurality of calibration standards, wherein each of the first plurality of calibration standards includes a different starting concentration of the analyte polynucleotide and a substantially constant concentration of the internal calibrator. There also is the step (b) of determining indicia of amplification for the analyte polynucleotide and the internal calibrator that co-amplified in each of the first plurality of calibration standards in step (a). There also is the step (c) of normalizing indicia of amplification determined for the analyte polynucleotide to indicia of amplification determined for the internal calibrator for each of the first plurality of calibration standards. There also is the step (d) of preparing a first calibration curve that relates normalized indicia of amplification for analyte polynucleotide as a function of the different starting concentrations of analyte polynucleotide for each of the first plurality of calibration standards. There also is the step (e) of co-amplifying, in a second plurality of real-time nucleic acid amplification reactions, the analyte polynucleotide and the internal calibrator contained in each of a second plurality of calibration standards, wherein each of the second plurality of calibration standards includes a different starting concentration of the analyte polynucleotide and said substantially constant concentration of the internal calibrator. There also is the step (f) of determining indicia of amplification for the analyte polynucleotide and the internal calibrator that co-amplified in each of the second plurality of calibration standards in step (e). There also is the step (g) of normalizing indicia of amplification determined for the analyte polynucleotide to indicia of amplification determined for the internal calibrator for each of the second plurality of calibration standards. There also is the step (h) of preparing a second calibration curve that relates normalized indicia of amplification for analyte polynucleotide as a function of the different starting concentrations of analyte polynucleotide for each of the second plurality of calibration standards. There also is the step (i) of preparing said kit as a packaged combination including: (1) an adjustment calibrator including a known amount of the analyte polynucleotide and said substantially constant concentration of the internal calibrator; and (2) a tangible embodiment of at least one of: coordinates of a pivot point indicating the intersection of the first and second calibration curves; coordinates of the pivot point and an equation for the first calibration curve; coordinates of at least two points from each of the first calibration curve and the second calibration curve; and the combination of a first equation defining the first calibration curve and a second equation defining the second calibration curve. According to a first generally preferred embodiment, there are the further steps of: transferring said tangible embodiment to a computer in communication with the local instrument; co-amplifying, in a real-time nucleic acid amplification reaction performed with the local instrument, the analyte polynucleotide and the internal calibrator of the an adjustment calibrator; and establishing with the computer, together with results from the real-time nucleic acid amplification reaction performed with the local instrument, an adjusted calibration curve for use with the local instrument. More preferably, the first plurality of real-time nucleic acid amplification reactions and the second plurality of real-time nucleic acid amplification reactions are performed using different instruments, and the local instrument is not used for performing either of the first or the second plurality of real-time amplification reactions. According to a second generally preferred embodiment, the first plurality of real-time nucleic acid amplification reactions and the second plurality of real-time nucleic acid amplification reactions are performed using different instruments, and the local instrument is not used for performing either of the first or the second plurality of real-time amplification reactions. According to a third generally preferred embodiment, step (a) and step (e) respectively include co-amplifying isothermally According to a fourth generally preferred embodiment, either: (1) the first and second plurality of real-time amplification reactions are conducted using different real-time instruments; or (2) the first and second plurality of real-time amplification reactions are conducted using different reaction compositions, and the first calibration curve and the second calibration curve are non-identical. According to a fifth generally preferred embodiment, the packaged combination of step (i) includes the tangible embodiment of coordinates of the pivot point indicating the intersection of the first and second calibration curves. According to a sixth generally preferred embodiment, the packaged combination of step (i) includes the tangible embodiment of coordinates of the pivot point and the equation for the first calibration curve. According to a seventh generally preferred embodiment, the packaged combination of step (i) includes the tangible embodiment of coordinates of at least two points from each of the first calibration curve and the second calibration curve. According to an eighth generally preferred embodiment, the packaged combination of step (i) includes the tangible embodiment of the combination of the first equation defining the first calibration curve and the second equation defining the second calibration curve.

Another aspect of the invention relates to a method of re-calibrating a local instrument that quantifies an analyte polynucleotide in a nucleic acid amplification assay, wherein the local instrument amplifies nucleic acids and monitors synthesis of amplification products as amplification is occurring. The method includes the step (a) of obtaining, in a machine-readable format, a first calibration curve that relates indicia of amplification for a plurality of analyte polynucleotide standards normalized to indicia of amplification for a fixed amount of an internal calibrator that co-amplified therewith as a function of starting amounts of the analyte polynucleotide in amplification reactions of the nucleic acid amplification assay. There also is the step (b) of co-amplifying, in a first plurality of real-time amplification reactions performed with the local instrument, the analyte polynucleotide and the internal calibrator contained in each of a first plurality of calibration standards, wherein each of the first plurality of calibration standards includes different known starting amounts of the analyte polynucleotide and a constant amount of the internal calibrator, whereby indicia of amplification for the analyte polynucleotide and the internal calibrator are determined for each of the first plurality of real-time amplification reactions. There also is the step (c) of establishing a local calibration curve that specifies values for indicia of amplification determined for the analyte polynucleotide normalized to indicia of amplification for the internal calibrator that co-amplified therewith in the first plurality of real-time amplification reactions as a function of values of starting amounts of the analyte polynucleotide used in the amplification reactions, wherein the local calibration curve is electronically stored in a computer in communication with the local instrument. There also is the step (d) of determining the intersection of the first calibration curve and the local calibration curve, thereby identifying a pivot point common to both of the first and the local calibration curves. There also is the step (e) of obtaining an adjustment calibrator including a known amount of the analyte polynucleotide and said constant amount of the internal calibrator. There also is the step (f) of co-amplifying, in a real-time amplification reaction performed with the local instrument, the analyte polynucleotide and the internal calibrator of the adjustment calibrator, whereby indicia of amplification for the analyte polynucleotide and the internal calibrator of the adjustment calibrator are determined. There also is the step (g) of normalizing indicia of amplification determined for the analyte polynucleotide to indicia of amplification for the internal calibrator determined for the adjustment calibrator. There also is the step (h) of re-calibrating the local instrument for the nucleic acid amplification assay by establishing, with the computer, an adjusted calibration curve that includes: (1) coordinates of a first point determined by the known amount of the analyte polynucleotide of the adjustment calibrator, and by the normalized indicia of amplification for the analyte polynucleotide determined for the adjustment calibrator; and (2) coordinates of the pivot point determined in step (d). According to a first general embodiment, there is the further step of, after step (c) and before step (f), of quantifying the analyte polynucleotide contained in a test sample following amplification in the nucleic acid amplification assay by comparing a normalized indicia of amplification value determined for the test sample with the local calibration curve. In a more highly preferred embodiment, there is yet the further step of, after step (h), quantifying the analyte polynucleotide contained in a test sample following amplification in the nucleic acid amplification assay by comparing a normalized indicia of amplification value determined for the test sample with the adjusted calibration curve. According to a second general embodiment, there is the further step of, after step (h), quantifying the analyte polynucleotide contained in a test sample following amplification in the nucleic acid amplification assay by comparing a normalized indicia of amplification value determined for the test sample with the adjusted calibration curve. According to a third general embodiment, the first calibration curve, the local calibration curve, and the adjusted calibration curve are all linear calibration curves defined by different linear equations. According to a fourth general embodiment, the first calibration curve is not determined by a process that includes performing real-time amplification reactions with the local instrument. According to a fifth general embodiment, the first calibration curve is determined by a process that includes performing real-time amplification reactions with the local instrument, and real-time amplification reactions used in the process include reaction compositions different from the first plurality of real-time amplification reactions so that the first calibration curve and the local calibration curve are not identical. According to a sixth general embodiment, the adjusted calibration curve is established using said first point and said pivot point, and without using data points resulting from amplification of calibration standards including the analyte polynucleotide in any amount other than the known amount of the analyte polynucleotide of the adjustment calibrator. According to a seventh general embodiment, the machine-readable format used for obtaining the first calibration curve in step (a) includes a machine-readable barcode. According to an eighth general embodiment, step (b) and step (f) include co-amplifying isothermally.

DETAILED DESCRIPTION

Introduction

The techniques, apparatus, and software products disclosed herein are useful for quantifying nucleic acids on real-time platforms (i.e., wherein reaction product synthesis is monitored as a function of time or cycle number). Generally speaking, the disclosed approaches employ two different reference calibration curves (e.g., equations therefor) for a single real-time assay. The reference calibration curves may differ by virtue of having been established on two different real-time instruments, or by virtue of reactions having been subject to different levels of inhibition on the same instrument or a different instrument. In a general application, the approach relies on maintaining, at all levels of input target, a constant relative relationship between the dual reference calibration curves and a single data point to be used for calibrating or re-calibrating a local instrument. Such a single data point may result from the use of an adjustment calibrator on a local instrument to be used for quantifying nucleic acid target amounts present in test samples. The approach applies to both linear and non-linear calibration curves. Particular embodiments of the approach employ a point of intersection (i.e., referred to below as a "pivot point") between the dual reference curves in combination with the single data point generated using an end-user's instrument to result in a complete calibration curve that can be used on the end-user's instrument.

Indeed, certain aspects of the disclosed approach are based on the observation that differences between one calibration plot and another, as may result from a re-calibration procedure on the same or a different instrument, are due to rotation about a fixed pivot-point. This applies to linear and non-linear calibration plots. As introduced above, and as discussed in more detail below, the pivot point is identified by the intersection of more than one calibration curve.

Disclosed herein is an internal calibration approach that employs results determined on an end-user's instrument in combination with a stored pivot point on a calibration plot. Optionally, the pivot point can be determined on the end-user's instrument and then stored for later use on that same instrument. Alternatively, the pivot point can be determined using one or more instruments (e.g., at a kit manufacturer's location), and then provided for use on the end-user's instrument. The disclosed approach advantageously facilitates production of a full calibration curve for nucleic acid quantitation using as few as a single nucleic acid calibration standard. Too, the approach simplifies workflow, and is more cost-effective than production of a complete calibration curve using a full set of calibrators each time a re-calibration procedure is needed. Still further, the approach provides outstanding quantitation over an extended dynamic range, and accommodates the use of aged or partially degraded reagents.

Particularly useful systems and methods will be capable of reproducing a complete calibration curve using a minimal number of calibration standards. Indeed, by the approach detailed herein, outstanding results have been achieved using only a single calibration standard to recreate a complete calibration curve. This can involve first establishing a calibration reference curve, which may be a linear or non-linear calibration curve, by the use of a plurality of calibration standards, each having a different amount of analyte polynucleotide standard and the same constant amount of internal calibrator (i.e., "IC"). Next, a point on the reference curve can be identified for use as a pivot point. Results from an amplification reaction performed using a calibration standard on an end-user's instrument can then be used to determine a target/IC threshold ratio value, thereby establishing a "local" (e.g., produced by an end-user) data point. In accordance with certain procedures, at least one point from the calibration reference curve is rotated by a mathematical transformation about the pivot point by an angle determined using the local data point, the pivot point, and one or more points on the reference curve. The rotationally transformed data point (i.e., the data point having been "rotated") is then used to create an adjusted calibration curve, for example by use in combination with the pivot point, or by use in combination with a plurality of similarly rotationally transformed data points from the calibration reference curve. In yet a different procedure, the pivot point and a point resulting from amplification of a single adjustment calibrator that has not undergone rotational transformation are used in combination to create an adjusted calibration curve. Finally, there is a step for quantifying target amounts present in test samples on the end-user instrument using the adjusted calibration curve.

According to one embodiment, a master calibration curve is prepared using results (e.g., normalized threshold values for amplified target and IC) from two or more amplification reactions performed using different calibration standards on a first instrument that amplifies nucleic acids and monitors amplicon production as a function of time or cycle number. Threshold values for target nucleic acid in the calibration standards are normalized to threshold values for IC determined for the same reactions, for example by division to result in ratios. The ratio value calculated for each of the two or more calibration reactions is then plotted (e.g., using an electronic spreadsheet) as a function of the starting amount of target input into the reaction. In some preferred instances, the calibration plot established is a linear calibration plot. In other preferred instances, the calibration plot established is a non-linear calibration plot.

A re-calibration procedure can be preformed using as few as one calibration standard having a known starting copy level of target nucleic acid, and the same constant amount of IC as employed in the reactions used to establish the two calibration curves that can be used to establish the pivot point. Determining and normalizing threshold values for target and IC in the real-time amplification reaction yields one point that can be used in combination with the equations for the two fitted calibration curves, or simply in combination with the pivot point to generate the full calibration plot.

As indicated above, there are different ways in which the pivot point can be used in combination with a second point to generate the calibration plot. In a first instance, the pivot point and ratio value determined for the calibration standard are both generated on the same instrument (e.g., the "first" instrument). In a second case, the fixed point and ratio value determined for the calibration standard are generated on different instruments. In both cases, the technique advantageously corrects calibration plots to account for aged reagents, including reagents that have been cycled on and off a particular instrument several times. As well, the technique does not depend on determination of amplification efficiencies. Still further, it is not required that the copy level or amount of IC included in each reaction is known. However, the IC copy level or amount in each reaction should be the same.

Definitions

The following terms have the following meanings for the purpose of this disclosure, unless expressly stated to the contrary herein.

As used herein, "polynucleotide" means either RNA, DNA, or a chimeric molecule containing both RNA and DNA. The term also embraces molecules containing nucleotide analogs of RNA or DNA.

By "analyte polynucleotide" or "analyte nucleic acid" is meant a polynucleotide of interest that is to be quantified. Generally speaking, analyte nucleic acids will be found in test samples. The genome of a particular virus would exemplify an analyte polynucleotide.

As used herein, a "test sample" is any sample to be investigated for the presence of a particular polynucleotide sequence. Test samples include any tissue or polynucleotide-containing material obtained from a human, animal, environmental, or laboratory-derived or synthetic sample. Blood and urine are preferred examples of test samples.

By "analyte polynucleotide standard" is meant a composition comprising a known quantity of an analyte polynucleotide, or fragment thereof. For example, an HIV-1 analyte polynucleotide standard may contain a known number of copies of an HIV-1 genome, HIV-1 transcript, or in vitro synthesized transcript representing a portion of the viral genome.

By "calibration standard" is meant a composition that includes a known or predetermined amount analyte polynucleotide standard in combination with a known constant amount of an internal calibrator polynucleotide. Two different calibration standards can contain different amounts of analyte polynucleotide or a fragment thereof, but will contain the same amount of internal calibrator nucleic acid. The analyte polynucleotide of the analyte polynucleotide standard, and the internal calibrator nucleic acid will be distinguishable from each other, for example by having nucleotide base sequences that are different.

"Adjustment calibrators" are calibration standards used for conducting amplification reactions on a local instrument, where results obtained from those amplification reactions provide data for creating a calibration plot. For example, amplification of an adjustment calibrator may provide a data point that may be used in combination with a fixed-point to create a full calibration plot. Likewise, the data point provided by amplification of the adjustment calibrator may be used for adjusting a stored master curve or reference curve (i.e., so that an end user's system can be adjusted to give the same calibrated output as that of the system used to derive the master calibration curve).

An "amplicon" is a polynucleotide product of an amplification reaction, wherein a target nucleic acid sequence served as the template for synthesis of polynucleotide copies or amplification products.

By "amplification" or "nucleic acid amplification" or "in vitro nucleic acid amplification" and the like is meant any known procedure for obtaining multiple copies, allowing for RNA and DNA equivalents, of a target nucleic acid sequence or its complement or fragments thereof. Amplification of "fragments thereof" refers to production of an amplified nucleic acid containing less than the complete target region nucleic acid sequence or its complement. Such fragments may be produced by amplifying a portion of the target nucleic acid, for example, by using an amplification oligonucleotide that hybridizes to, and initiates polymerization from, an internal position of the target nucleic acid.

As used herein, the terms "coamplify" and "coamplifying" and variants thereof refer to a process wherein different target nucleic acid sequences are amplified in a single (i.e., the same) amplification reaction. For example, an analyte polynucleotide and an unrelated internal calibrator nucleic acid are "coamplified" when both nucleic acids are amplified in reactions taking place in a single tube, and when both amplification reactions share at least one reagent (e.g., deoxyribonucleotide triphosphates, enzyme, primer(s), etc.) in common.

As used herein, "thermal cycling" refers to repeated changes of temperature, (i.e., increases or decreases of temperature) in a reaction mixture. Samples undergoing thermal cycling may shift from one temperature to another, stabilize at that temperature, transition to a second temperature or return to the starting temperature. The temperature cycle may be repeated as many times as required to study or complete the particular chemical reaction of interest.

By "target" or "target nucleic acid" is meant a nucleic acid containing a sequence that is to be amplified, detected and quantified. A target nucleic acid sequence that is to be amplified preferably will be positioned between two oppositely disposed oligonucleotides, and will include the portion of the target nucleic acid that is complementary to each of the oligonucleotides.

By "target nucleic acid sequence" or "target sequence" or "target region" is meant a specific deoxyribonucleotide or ribonucleotide sequence comprising all or part of the nucleotide sequence of a single-stranded nucleic acid molecule, and the deoxyribonucleotide or ribonucleotide sequence complementary thereto.

By "transcription-associated amplification" is meant any type of nucleic acid amplification that uses an RNA polymerase to produce multiple RNA transcripts from a nucleic acid template. Conventionally, these amplification reactions employ at least one primer having a 3'-end that can be extended by the activity of a DNA polymerase. One example of a transcription-associated amplification method, called "Transcription Mediated Amplification" (TMA), generally employs an RNA polymerase, a DNA polymerase, deoxyribonucleoside triphosphates, ribonucleoside triphosphates, and a promoter-containing oligonucleotide complementary to the target nucleic acid. Variations of TMA are well known in the art as disclosed in detail in Burg et al., U.S. Pat. No. 5,437,990; Kacian et al., U.S. Pat. Nos. 5,399,491 and 5,554,516; Kacian et al., PCT No. WO 93/22461; Gingeras et al., PCT No. WO 88/01302; Gingeras et al., PCT No. WO 88/10315; Malek et al., U.S. Pat. No. 5,130,238; Urdea et al., U.S. Pat. Nos. 4,868,105 and 5,124,246; McDonough et al., PCT No. WO 94/03472; and Ryder et al., PCT No. WO 95/03430. Other transcription-associated amplification methods employing only a single primer that can be extended by a DNA polymerase, as disclosed in the U.S. patent application having Ser. No. 11/213,519 are particularly embraced by the definition and are highly preferred for use in connection with the method disclosed herein.

As used herein, an "oligonucleotide" or "oligomer" is a polymeric chain of at least two, generally between about five and about 100, chemical subunits, each subunit comprising a nucleotide base moiety, a sugar moiety, and a linking moiety that joins the subunits in a linear spacial configuration. Common nucleotide base moieties are guanine (G), adenine (A), cytosine (C), thymine (T) and uracil (U), although other rare or modified nucleotide bases able to hydrogen bond are well known to those skilled in the art. Oligonucleotides may optionally include analogs of any of the sugar moieties, the base moieties, and the backbone constituents. Preferred oligonucleotides of the present invention fall in a size range of about 10 to about 100 residues. Oligonucleotides may be purified from naturally occurring sources, but preferably are synthesized using any of a variety of well known enzymatic or chemical methods.

By "amplification oligonucleotide" or "amplification oligomer" is meant an oligomer that hybridizes to a target nucleic acid, or its complement, and participates in a nucleic acid amplification reaction. Examples of amplification oligomers include primers that contain a 3' end that is extended as part of the amplification process, but also include oligomers that are not extended by a polymerase (e.g., a 3' blocked oligomer) but may participate in, or facilitate efficient amplification from a primer. Preferred size ranges for amplification oligomers include those that are about 10 to about 80 nucleotides long, or 10 to about 60 nucleotides long and contain at least about 10 contiguous bases, and more preferably at least 12 contiguous bases that are complementary to a region of the target nucleic acid sequence (or a complementary strand thereof). The contiguous bases are preferably at least about 80%, more preferably at least about 90%, and most preferably about 100% complementary to the target sequence to which amplification oligomer binds. An amplification oligomer may optionally include modified nucleotides or analogs, or additional nucleotides that participate in an amplification reaction but are not complementary to or contained in the target nucleic acid. An amplification oligomer that is 3' blocked but capable of hybridizing to a target nucleic acid and providing an upstream promoter sequence that serves to initiate transcription is referred to as a "promoter provider" oligomer.

A "primer" is an amplification oligomer that hybridizes to a template nucleic acid and has a 3' OH end that can be extended by a DNA polymerase. The 5' region of the primer may be non-complementary to the target nucleic acid (e.g., a promoter sequence), resulting in an oligomer referred to as a "promoter-primer." Those skilled in the art will appreciate that any oligomer that can function as a primer can be modified to include a 5' promoter sequence, and thus could function as a promoter-primer. Similarly, any promoter-primer can be modified by removal of, or synthesis without, a promoter sequence and still function as a primer.

As used herein, a "set" of amplification oligonucleotides refers to a collection of two or more amplification oligonucleotides that cooperatively participate in an in vitro nucleic acid amplification reaction to synthesize amplicons.

As used herein, a "probe" is an oligonucleotide that hybridizes specifically to a target sequence in a nucleic acid, preferably in an amplified nucleic acid, under conditions that promote hybridization, to form a detectable hybrid.

As used herein, "time-dependent" monitoring of nucleic acid amplification, or monitoring of nucleic acid amplification in "real-time" refers to a process wherein the amount of amplicon present in a nucleic acid amplification reaction is measured as a function of reaction time or cycle number, and then used to determine a starting amount of template that was present in the reaction mixture at the time the amplification reaction was initiated. For example, the amount of amplicon can be measured prior to commencing each complete cycle of an amplification reaction that comprises thermal cycling, such as PCR. Alternatively, isothermal amplification reactions that do not require physical intervention to initiate the transitions between amplification cycles can be monitored continuously, or at regular time intervals to obtain information regarding the amount of amplicon present as a function of time.

As used herein, a "growth curve" refers to the characteristic pattern of appearance of a synthetic product, such as an amplicon, in a reaction as a function of time or cycle number. A growth curve is conveniently represented as a two-dimensional plot of time (x-axis) against some indicator of product amount, such as a fluorescence measurement (y-axis). Some, but not all, growth curves have a sigmoid-shape.

As used herein, the "baseline phase" of a growth curve refers to the initial phase of the curve wherein the amount of product (such as an amplicon) increases at a substantially constant rate, this rate being less than the rate of increase characteristic of the growth phase (which may have a log-linear profile) of the growth curve. The baseline phase of a growth curve typically has a very shallow slope, frequently approximating zero.

As used herein, the "growth phase" of a growth curve refers to the portion of the curve wherein the measurable product substantially increases with time. Transition from the baseline phase into the growth phase in a typical nucleic acid amplification reaction is characterized by the appearance of amplicon at a rate that increases with time. Transition from the growth phase to the plateau phase of the growth curve begins at an inflection point where the rate of amplicon appearance begins to decrease.

As used herein, the "plateau phase" of a triphasic growth curve refers to the final phase of the curve. In the plateau phase, the rate of measurable product formation generally is substantially lower than the rate of amplicon production in the log-linear phase, and may even approach zero.

As used herein, the phrase "indicia of amplification" refers to features of real-time run curves which indicate a predetermined level of progress in nucleic acid amplification reactions. Such indicia are commonly determined by mathematical analysis of run curves, sometimes referred to as "growth curves," which display a measurable signal (such as a fluorescence reading) whose intensity is related to the quantity of an amplicon present in a reaction mixture as a function of time, cycle number, etc.

As used herein, the phrase "threshold-based indicia of amplification" refers to indicia of amplification that measure the time or cycle number when a growth curve signal crosses an arbitrary value or threshold. TTime determinations are examples of threshold-based indicia of amplification, while TArc and OTArc determinations are examples of non-threshold-based indicia of amplification.

As used herein, the phrase "time-dependent" indicia of amplification refers generally to indicia of amplification (e.g., a reaction progress parameter) that are measured in time units (e.g., minutes). Time-dependent indicia of amplification are commonly used for monitoring progress in isothermal nucleic acid amplification reactions that are not characterized by distinct "cycles." All of TTime, TArc and OTArc are examples of time-dependent indicia of amplification.

As used herein, an "internal calibrator" (sometimes "IC" herein) is a polynucleotide that can be amplified in an in vitro nucleic acid amplification reaction, and that is distinguishable from an analyte polynucleotide that coamplified in the same reaction. "Internal" means that the calibrator polynucleotide is amplified, detected and quantified within the same reaction mixture as the analyte polynucleotide, or fragment thereof. Generally speaking, the amount or concentration of the internal calibrator will be constant in different reactions used for preparing calibration curves, and for quantifying the analyte polynucleotide. Preferably, the constant amount or concentration of internal calibrator will be a known amount of internal calibrator, or a known concentration of internal calibrator. In certain preferred embodiments, the internal calibrator and the analyte polynucleotide are coamplified in an in vitro nucleic acid amplification reaction using one or more different amplification oligomers or primers. For example, the analyte and internal calibrator polynucleotides employed in the working Examples detailed below were amplified using amplification oligonucleotides that were not shared. In other preferred embodiments, the internal calibrator and the analyte polynucleotide are coamplified in an in vitro nucleic acid amplification reaction using one or more identical amplification oligomers or primers.

As used herein, the phrase "as a function of" describes the relationship between a dependent variable (i.e., a variable that depends on one or more other variables) and an independent variable (i.e., a variable that may have its value freely chosen without considering the values of any other variables), wherein each input value for the independent variable relates to exactly one output value for the dependent variable. Conventional notation for an equation that relates a y-value (i.e., the dependent variable) "as a function of" an x-value (i.e., the independent variable) is $y=f(x)$.

As used herein, "optimizing" or "fitting" an equation refers to a process, as commonly practiced in mathematical modeling or curve fitting procedures, for obtaining numerical values for coefficients in an equation to yield an expression that "fits" or approximates experimental measurements. Typically, an optimized equation will define a best-fit curve.

As used herein, the terms "optimized equation," and "fitted equation" are alternative references to an equation containing fixed numerical values for coefficients as the result of an optimizing procedure. "Fitted" curves result from optimizing an equation.

By "local" is meant relating to an end-user. For example, a local instrument refers to an end-user's instrument. A local calibration plot refers to a calibration plot using results obtained by an end-user, for example by conducting an amplification reaction on the local instrument.

By "re-calibrate" or "re-calibration" is meant a calibration procedure or result subsequent to an earlier calibration procedure or result that is performed or obtained using the same instrument. For example, the first time a calibration procedure is performed using an instrument that amplifies nucleic acids and monitors amplicon synthesis as a function of cycle numbers or time (e.g., a real-time PCR instrument), two different calibration standards may be amplified and a calibration plot may result. The calibration plot may mathematically relate a ratio value as a function of the starting target amount input into the amplification reaction. A re-calibration procedure would employ that same instrument for producing a subsequent or updated calibration plot.

By "calibration plot" is meant a graphical or mathematical representation relating a quantity that can be measured for an amplification reaction (e.g., a ratio of measured threshold values for amplified target and internal calibrator) to a known amount of substrate input into the amplification reaction (e.g., the starting amount of target nucleic acid). A calibration plot preferably is established using computer spreadsheet software, and includes electronic representations of calibration results or information. "Calibration plot" and "calibration curve" are used interchangeably. It is to be understood that a calibration plot or curve can refer to linear and non-linear calibration curves.

As used herein, a "fixed-point" is a data point (e.g., having x- and y-coordinates) that can be used for establishing a calibration plot in a calibration or re-calibration procedure, where that data point does not change with time. The fixed-point may be determined and used on a single apparatus (e.g., a local instrument). Alternatively, the fixed-point may be determined using an apparatus at an assay kit manufacturer's site, and then used by a customer or end-user on a different apparatus.

As used herein, in the context of a calibration plot, a "pivot-point" is a fixed-point determined by the intersection of more than one calibration curve (including linear and non-linear curves). For example, the intersection of two linear calibration plots may define a pivot-point that is common to both calibration plots.

By "kit" is meant a packaged combination of materials, typically intended for use in conjunction with each other. Kits in accordance with the invention may include instructions or other information in a "tangible" form (e.g., printed information, electronically recorded on a computer-readable medium, or otherwise recorded on a machine-readable medium such as a bar code for storing numerical values).

By "consisting essentially of" is meant that additional component(s), composition(s) or method step(s) that do not materially change the basic and novel characteristics of the present invention may be included in the present invention. Any component(s), composition(s), or method step(s) that have a material effect on the basic and novel characteristics of the present invention would fall outside of this term.

Preferred Nucleic Acid Amplification Methods

Examples of amplification methods useful in connection with the present invention include, but are not limited to: Transcription Mediated Amplification (TMA), Single-Primer Nucleic Acid Amplification, Nucleic Acid Sequence-Based Amplification (NASBA), the Polymerase Chain Reaction (PCR), Strand Displacement Amplification (SDA), Self-Sustained Sequence Replication (3SR), DNA Ligase Chain Reaction (LCR) and amplification methods using self-replicating polynucleotide molecules and replication enzymes such as MDV-1 RNA and Q-beta enzyme. Methods for carrying out these various amplification techniques respectively can be found in U.S. Pat. No. 5,399,491, U.S. patent application Ser. No. 11/213,519, published European patent application EP 0 525 882, U.S. Pat. Nos. 4,965,188, 5,455,166, Guatelli et al., *Proc. Natl. Acad. Sci. USA* 87:1874-1878 (1990), International Publication No. WO 89/09835, U.S. Pat. No. 5,472,840 and Lizardi et al., *Trends Biotechnol.* 9:53-58 (1991). The disclosures of these documents which describe how to perform nucleic acid amplification reactions are hereby incorporated by reference.

Amplification reactions that require only a single extendable primer are particularly preferred for use in connection with the disclosed algorithm. These reactions include transcription-associated amplification systems that employ a single extendable primer in combination with a 3'-blocked oligonucleotide that cannot be extended by a nucleic acid polymerase. Methods for carrying out such amplification reactions are, for example, detailed in U.S. patent application Ser. No. 11/213,519.

Examples of Useful Indicia of Amplification

A variety of indicia of amplification can be used in connection with the disclosed method. For example, mathematical and computing techniques that will be familiar to those having an ordinary level of skill in the art can be used to identify the time of occurrence of the maximum of the first derivative, or the time of occurrence of the maximum of the second derivative of a real-time run curve. Approaches for determining these features of a growth curve have been detailed by Wittwer et al., in U.S. Pat. No. 6,503,720, the disclosure of which is incorporated by reference herein. Other useful approaches involve calculating a derivative of a growth curve, identifying a characteristic of the growth curve, and then determining the threshold time or cycle number corresponding to the characteristic of the derivative. Such techniques have been disclosed in U.S. Pat. No. 6,783,934, the disclosure of which is incorporated by reference. Still other useful indicia of amplification include "TTime" and "TArc." Notably, different approaches for determining TArc values employ directionally similar vectors (i.e., resulting in a value identified simply by "TArc"), and directionally opposed vectors (i.e., resulting in a value identified as "OTArc"). Still other techniques involve identifying cycle threshold (e.g., "Ct") values as the time or cycle number during a reaction at which a signal, preferably a fluorescent signal, equals a static threshold (e.g., a predetermined static threshold value). General descriptions of these methods latter are given below.

Methods of Determining TTime Values

Simply stated, TTime values estimate the time at which a particular threshold indicating amplicon production is passed in a real-time amplification reaction. The algorithm for calculating and using TTime values has been described in the U.S. patent application identified by Ser. No. 60/659,874, the disclosure of which is incorporated by reference. According to this algorithm, a curve fit procedure is applied to normalized and background-adjusted data. Although any of the well-known curve fit methodologies may be employed, in a preferred embodiment, a linear least squares ("LLS") curve fit is employed. The curve fit is performed for only a portion of the data between a predetermined low bound and high bound. The ultimate goal, after finding the curve which fits the data, is to estimate the time corresponding to the point at which the curve or a projection thereof intersects a predetermined static threshold value. In one embodiment, the threshold for normalized data is 0.11. The high and low bounds are determined empirically as that range over which curves fit to a variety of control data sets exhibit the least variability in the time associated with the given threshold value. In one embodiment, the low bound is 0.04 and the high bound is 0.36. The curve is fit for data extending from the first data point below the low bound through the first data point past the high bound. Next, there is made a determination whether the slope of the fit is statistically significant. For example, if the p value of the first order coefficient is less than 0.05, the fit is considered significant, and processing continues. If not, processing stops. Alternatively, the validity of the data can be determined by the $R^2$ value. The slope m and intercept b of the linear curve $y=mx+b$ are determined for the fitted curve. With that information, TTime can be determined.

Methods of Determining TArc Values

Time-dependent indicia of amplification referred to as "TArc" and "OTArc" are determined using vector-based analyses of real-time run curves. The TArc value identifies the point in time at which a growth curve begins to curve or "inflect" upward. This determined point can be used for creating a standard curve, or for establishing a parameter of an amplification reaction that relates to the amount or concentration of an analyte polynucleotide in a test sample. The vector analysis is most conveniently carried out using growth curves having data points distributed over substantially uniform time intervals. Detailed presentations concerning the determination and use of TArc and OTArc values appear in the U.S. Pat. No. 7,739,054, which is incorporated by reference herein.

Preferred Systems and Apparatus

The methods disclosed herein are conveniently implemented using a computer or similar processing device ("computer" hereafter). In different preferred embodiments, software or machine-executable instructions for performing an algorithm can be loaded or otherwise held in a memory component of a freestanding computer, or in a memory component of a computer linked to a device used for monitoring, preferably as a function of time, the amount of a product undergoing analysis. In a highly preferred embodiment, software for executing the calibration algorithm is held in a memory component of a computer that is linked to, or that is an integral part of a device capable of monitoring the amount of an amplicon present in a reaction mixture as a function of time.

Indeed, either or both of a controller system for controlling a real-time amplification device and/or the detection system of the real-time amplification device can be coupled to an appropriately programmed computer which functions to instruct the operation of these instruments in accordance with preprogrammed or user input instructions. The computer preferably also can receive data and information from these instruments, and interpret, manipulate and report this information to the user.

In general, the computer typically includes appropriate software for receiving user instructions, either in the form of user input into a set of parameter fields, or in the form of preprogrammed instructions (e.g., preprogrammed for a variety of different specific operations). The software then converts these instructions to appropriate language for instructing the operation of the real-time amplification controller to carry out the desired operation. The computer also is capable of receiving data from the one or more sensors/detectors included within the system, and interprets the data in accordance with the programming. The system preferably includes software that correlates a feature of a growth curve representing the quantity of amplified copies of the nucleic acid of interest as a function of time, as detected by the detector, to the number of copies of the nucleic acid of interest present in a test sample.

Preferably, when the computer used for executing the disclosed calibration algorithm is an integral component of an apparatus for performing and analyzing real-time nucleic acid amplification reactions, the apparatus preferably comprises a temperature-controlled incubator, a detection device for collecting signals, an analyzing device (e.g., a computer or processor) for analyzing signals and an output device for displaying data obtained or generated by the analyzing device. The analyzing device may be connected to the temperature-controlled incubator through an input device known in the art, and/or connected to an output device known in the art for data display. In one embodiment, the temperature-controlled incubator is capable of temperature cycling.

Generally speaking, the various components of an apparatus for performing the real-time nucleic acid amplification useful in connection with the disclosed methods will be conventional components that will be familiar to those having an ordinary level of skill in the art. The temperature-controlled incubator used to perform and analyze real-time nucleic acid amplification may be of a conventional design which can hold a plurality of reaction tubes, or reaction samples in a temperature-controlled block in standard amplification reaction tubes or in wells of a multiwell plate. In one aspect, the detection system is suitable for detecting optical signals from one or more fluorescent labels. The output of the detection system (e.g., signals corresponding to those generated during the amplification reaction) can be fed to the computer for data storage and manipulation. In one embodiment, the system detects multiple different types of optical signals, such as multiple different types of fluorescent labels and has the capabilities of a microplate fluorescence reader. The detection system is preferably a multiplexed fluorimeter containing an excitation light source, which may be a visible light laser or an ultraviolet lamp or a halogen lamp, a multiplexer device for distributing the excitation light to the individual reaction tubes and for receiving fluorescent light from the reaction tubes, a filtering means for separating the fluorescence light from the excitation light by their wavelengths, and a detection means for measuring the fluorescence light intensity. Preferably, the detection system of the temperature-controlled incubator provides a broad detection range that allows flexibility of fluorophore choice, high sensitivity and excellent signal-to-noise ratio. Optical signals received by the detection system are generally converted into signals which can be operated on by the processor to provide data which can be viewed by a user on a display of a user device in communication with the processor. The user device may comprise a user interface or may be a conventional commercially available computer system with a keyboard and video monitor. Examples of data which can be displayed by the user device include amplification plots, scatter plots, sample value screens for all the tubes or reaction vessels in the assembly and for all labels used, an optical signal intensity screen (e.g., fluorescent signal intensity screen), final call results, text reports, and the like.

Computer Program Products

Included within the scope of the invention are software-based products (e.g., tangible embodiments of software for instructing a computer to execute various procedural steps) that can be used for performing the data processing method. These include software instructions stored on computer-readable media, such as magnetic media, optical media, "flash" memory devices, and computer networks. As well, the invention embraces a system or an apparatus that amplifies nucleic acids, detects nucleic acid amplification products, and processes results to indicate a quantitative result for target in a test sample. Although the various components of the apparatus preferably function in a cooperative fashion, there is no requirement for the components to be part of an integrated assembly (e.g., on a single chassis). However, in a preferred embodiment, components of the apparatus are connected together. Included within the meaning of "connected" are connections via wired and wireless connections.

Particularly falling within the scope of the invention is an apparatus or system that includes a computer linked to a device that amplifies nucleic acids and monitors amplicon synthesis as a function of cycle number or time, where the computer is programmed to execute the quantitative algorithm disclosed herein. An exemplary system in accordance with the invention will include a temperature-controlled incubator, and a fluorimeter capable of monitoring and distinguishing at least two wavelengths of fluorescent emissions. These emissions may be used to indicate target amplicon synthesis, and IC amplicon synthesis.

Single-Point Calibration and Re-Calibration Procedures Facilitate Random Access Format Modern "random-access" devices that quantify target nucleic acids in test samples using real-time amplification advantageously will permit an end user to cycle reagents on-and-off the instrument multiple times. Reagents for a single kit may, therefore, be loaded/unloaded several times before a kit is used completely. As a result, it may be necessary to re-run the calibration plot (e.g., each time the kit is loaded onto the instrument). Significant kit resources could be expended to accommodate the random-access feature if two calibrators were employed for each re-calibration procedure. However, this process can be simplified using the "single-point system re-calibration" approach disclosed herein.

In one preferred embodiment, dual reference calibration curves (e.g., master curves) are prepared by an assay manufacturer and then provided to a customer or end-user in connection with purchase of a kit. As an alternative to providing full reference curves or plots (e.g., equations therefor, and electronic representations thereof), the end-user may be provided with a pivot point determined from the intersection of the two curves. Of course, in instances wherein reference curves never intersect, equations for the curves can be provided.

As an alternative, one or both of the dual reference curves to be used for internal calibration adjustment may be prepared by the end-user. Of course, this will entail additional effort, at least initially, on the part of the end-user. Perhaps balancing this is the possible benefit of creating reference curves specific to a particular instrument.

In certain embodiments of the re-calibration procedure, a conventional calibration plot can be established by an end-user on a local instrument the first time a kit is used. This may involve performance of two calibration reactions. Time-dependent amplification for Target and IC in both calibration reactions can be determined and normalized, for example by dividing the indicia for Target by the indicia for IC that amplified in the same reaction. The two points can be used to establish a calibration plot that can be used immediately for quantifying target nucleic acids in test samples. Separately, the resulting calibration plot can be projected to identify the intersection with a stored master curve, thereby identifying a single pivot point that can be used for preparing re-calibration plots. Although not used for creating the initial calibration plot, the identified pivot point can be stored for use in conjunction with re-calibration procedures.

System re-calibration can be carried out using as few as a single adjustment calibrator. Given availability of a pivot point, indicia of amplification for Target and coamplified IC for the adjustment calibrator can be normalized to give a ratio value, and the normalized result used in combination with the pivot point by one of the techniques illustrated herein to result in a complete calibration curve. Alternatively, given availability of dual reference curves, the same normalized result from a single adjustment calibrator can be used for establishing a complete calibration curve by requiring a constant proportional relationship between the adjustment calibrator data point and the dual reference curves.

Generally speaking, there is clear advantage to performing calibration and re-calibration procedures using minimal resources to facilitate periodic instrument calibration.

Preferred Methods of Selecting Reference Calibration Curves and Pivot Points

Pivot points employed in the disclosed calibration approach can be determined in a number of different ways. In preferred approaches, the fixed point is identified as the intersection of two different calibration curves for the same real-time nucleic acid amplification and detection assay. In one preferred method, the different calibration curves to be intersected are generated using calibration data produced on one or more instruments. For example, one or more instruments at an assay manufacturer's site may be used to determine the fixed point which is then provided to an end-user of the kit for use on the end-user's instrument (i.e., an instrument different from the one(s) used for making the determination). Alternatively, the fixed point can be determined on the same instrument that is used for quantifying target nucleic acid in samples undergoing testing. In this instance, the end user may carry out amplification reactions on a single instrument, use the resulting data to produce a plurality of calibration plots, and then use the different calibration plots to determine the fixed point. If more than two calibration plots are available, it may be desirable to determine the fixed point using information from multiple intersections.

The two calibration curves used in the procedure described herein preferably differ from each other with respect to the level of inhibition of amplification reactions used for generating data and preparing curves. Simply stated, one of the calibration curves reflects a greater level of inhibition relative to the other. Preparing the curves may involve omission or depletion of a reaction component, or inclusion of an amplification inhibitory substance in one set of amplification reactions. Generally speaking, inhibition of amplification reactions is evidenced by delays in threshold time values (e.g., Ct values, TTime values, TArc values, etc.). One example approach that can be used for inhibiting amplification reactions involves use of aged, or partially degraded reagents. Other inhibitory agents that may be used will be known to those having an ordinary level of skill in the art (see EP 6640828B1 (Higuchi)).

WORKING EXAMPLES

The first Example demonstrates how local and stored calibration reference curves, used for quantifying nucleic acids processed by real-time amplification, were substantially related as rotational transforms of each other. The Example specifically illustrates how the point of intersection of two calibration curves could be used as a pivot point for curve adjustment procedures. Specifically illustrated is a method by which the pivot point could be used in combination with a single, experimentally determined data point resulting from use of one calibration standard to approximate a full calibration plot by mathematically rotating one or more points of a stored reference curve about the pivot point by an angle appropriate to yield an adjusted calibration curve fitted to include the experimentally determined data point and the pivot point. In preferred embodiments of the calibration adjustment procedure described below, only a single data point from a stored reference curve is mathematically rotated about the pivot point, and that rotationally transformed data point used in combination with the pivot point to approximate a full local calibration curve. In other preferred embodiments, a plurality of experimentally determined data points resulting from a plurality of reactions comprising different calibration standards are used to approximate a full calibration plot by mathematically rotating individual points from the stored reference curve about the pivot point, and then fitting a curve to the rotationally transformed data points.

Example 1 describes how a stored calibration reference curve prepared using three different automated real-rime nucleic acid amplification instruments, and a second calibration curve produced on a different instrument (i.e., a "local" instrument representing an end-user's instrument) were related to each other as rotational transforms. In this instance, the two calibration curves were non-linear curves. Rather than adjusting the reference curve equation directly, the rotational transformation is illustrated below using individual data points and fitting of an equation to the rotational transform.

Example 1

Non-Linear Local and Stored Calibration Reference Curves are Substantially Related as Rotational Transforms of Each Other Data points representing ratio values (i.e., $TTime_{Target}/TTime_{IC}$ values) for each of a stored reference curve and a local calibration curve were taken from an electronic version of FIG. 12 in U.S. Pat. No. 7,930,106. The master curve data had been established using results averaged from three instruments, while the local curve had been established using results from a fourth instrument that was not used for producing the master curve. Values presented below in Table 1 are consistent with the graphical disclosure in U.S. Pat. No. 7,930,106, wherein the master curve extends on the horizontal axis from $10^1$ to $10^7$ copies/sample of analyte polynucleotide standard, and the local curve extends from $10^2$ to $10^8$ copies/sample of analyte polynucleotide standard.

TABLE 1

Raw Data for Rotational Transformation Study

| Target Input (log copies/sample) | Ratio from Master Curve | Ratio from Local Curve |
|---|---|---|
| 1.00 | 2.6400 | N/A |
| 2.00 | 2.0758 | 3.1269 |
| 3.00 | 1.6831 | 2.3336 |
| 4.00 | 1.3803 | 1.7881 |
| 5.00 | 1.1342 | 1.3549 |
| 6.00 | 0.9274 | 1.0706 |
| 7.00 | 0.7497 | 0.8522 |
| 8.00 | N/A | 0.6709 |

FIG. 1 shows a graph of data from Table 1, corresponding to target input levels of $10^2$ to $10^7$ copies/sample, plotted as a function of input target levels. Fitted exponential equations and $R^2$ values were determined using EXCEL electronic spreadsheet software (Microsoft Corporation, WA) and techniques that will be familiar to those having an ordinary level of skill in the art. The master curve and local curve shown in the figure were defined by Equation 1 ($R^2$ was 0.9998) and Equation 2 ($R^2$ was 0.9979), as follows.

Master Curve:

$$Y_{mc} = 3.1034 e^{-0.202 X} \quad \text{[Equation 1]}$$

Local Curve:

$$Y_{local} = 5.1312 e^{-0.26 X} \quad \text{[Equation 2]}$$

Equation 1 and Equation 2 were set equal to each other and solved to determine the point of identity (i.e., the pivot point). In this instance the point of identity had the coordinates: (8.6697, 0.5386).

Figure 2:
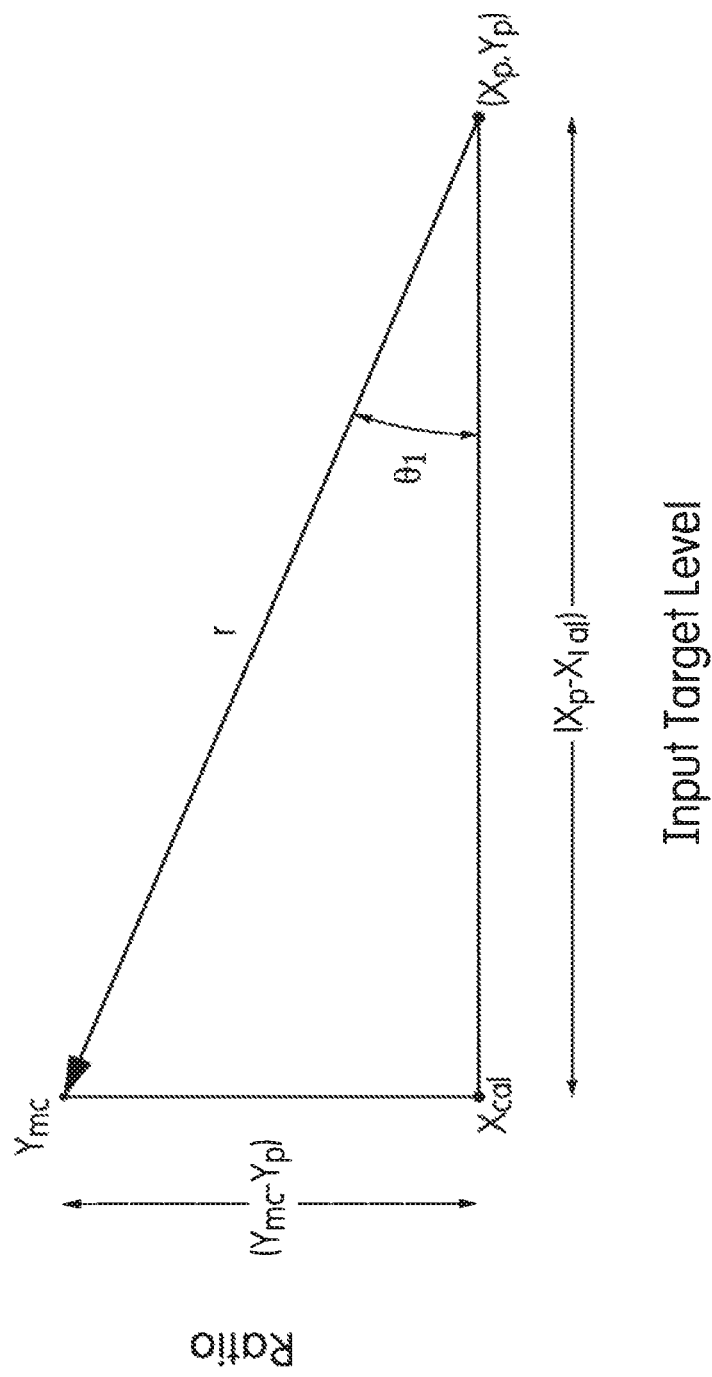
FIG. 2 is a diagram illustrating a vector having a magnitude (r), and extending from a pivot point ($X_p$, $Y_p$) to a point on a master calibration curve at a specified input target level ($X_{cal}$, $Y_{mc}$). The diagram also illustrates an approach for determining an angle ($\theta_1$).

Vectors extending from the pivot point to each of the points on the master curve that were to be rotationally transformed were next established. Distances (i.e., vector magnitudes) separating the pivot point and points on the master curve were determined by either of two methods. First, the Pythagorean Theorem (i.e., $a^2+b^2=c^2$) was used. In a second approach, now preferred, the magnitude of each vector was determined using the angle shown as "$\theta_1$" in FIG. 2. As indicated in the figure, $\theta_1$ is the angle between a vector drawn from the pivot point $(X_p, Y_p)$ to a data point on the master curve $(X_{cal}, Y_{mc})$, and a horizontal axis established at the vector origin (i.e., the pivot point). The relationship shown as Equation 3 was used for determining $\theta_1$.

$$\text{Tan } \theta_1 = (Y_{mc} - Y_p)/(X_p - X_{cal}) \quad \text{[Equation 3]}$$

The magnitude ("r"), or length of each vector was then calculated using Equation 4.

$$r = (Y_{mc} - Y_p)/\text{Sin } \theta_1 \quad \text{[Equation 4]}$$

Results from this procedure, carried out for samples amplified using input target levels of $10^2$ and $10^3$ copies/sample, are collected in Table 2. Notably, the vectors subsequently defined radii used for executing the rotational transformation about the pivot point by an angle determined using one of the entries in Table 2 as a simulated adjustment calibrator.

TABLE 2

Angles and Vector Magnitudes Calculated Using Master Curve Data and the Pivot Point

| Target Input (log copies/sample) | Ratio from Master Curve | $\theta_1$ (radians) | Vector Magnitudes ("r") (length units) |
|---|---|---|---|
| 2.00 | 2.0758 | 0.2265 | 6.8446 |
| 3.00 | 1.6831 | 0.1992 | 5.7841 |

To illustrate the rotational transformation procedure, results from amplification of the $10^3$ copies/sample calibration standard on the local instrument were used to simulate an adjustment calibrator, and to determine the angle of rotation for other points on the reference curve.

Figure 3:
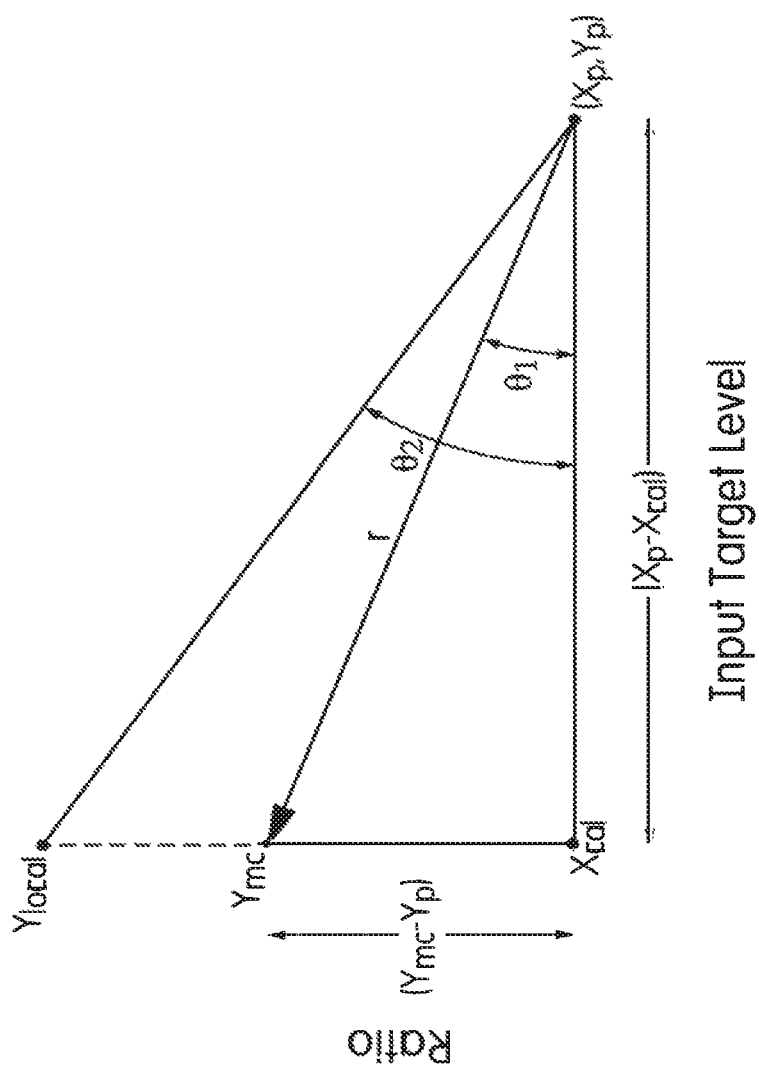
FIG. 3 is a diagram illustrating how data points for amplification of a calibration standard on a local instrument can be different from the corresponding value taken from a stored reference curve at a specified input target level. Also shown is the relationship between two angles ($\theta_1$ and $\theta_2$).

The process begins with determination of the angle (i.e., "$\theta_2$") between a ray extending from the pivot point $(X_p, Y_p)$ to the coordinate for the $10^3$ copies/sample adjustment calibrator $(X_{cal}, Y_{local})$ run on the end-user's instrument (e.g., taken from the local curve, above), and a horizontal axis established at the origin of the ray (i.e., the Y coordinate of the pivot point). FIG. 3 illustrates the graphical relationship among the data points representing: (a) the pivot point $(X_p, Y_p)$; (b) a point on the master curve corresponding to a particular input level of polynucleotide standard $(X_{cal}, Y_{mc})$; and (c) a result obtained using a calibration standard having the same amount of polynucleotide standard as the master curve data point $(X_{cal}, Y_{local})$. The relationship shown as Equation 5 was used for determining $\theta_2$.

$$\text{Tan } \theta_2 = (Y_{local} - Y_p)/(X_p - X_{cal}) \quad \text{[Equation 5]}$$

Data points of the master curve (i.e., either points used to create a fitted curve, or points falling on the fitted curve) can be rotated by an angle equivalent to the difference between the two angles, calculated above. This difference is expressed as follows.

$$\theta_2 - \theta_1 = \Delta \quad \text{[Equation 6]}$$

For each point to be rotationally transformed, the following coordinates were calculated.

$$X_{rot} = X_p - r \, \text{Cos}(\theta_1 + \Delta) \quad \text{[Equation 7]}$$

$$Y_{rot} = Y_p + r \, \text{Sin}(\theta_1 + \Delta) \quad \text{[Equation 8]}$$

In Equations 7 and 8 "$X_{rot}$" and "$Y_{rot}$" are the rotational transforms of the (X, Y) coordinates separated from the pivot point by a distance equal to the vector magnitude associated with that data point.

Figure 4:
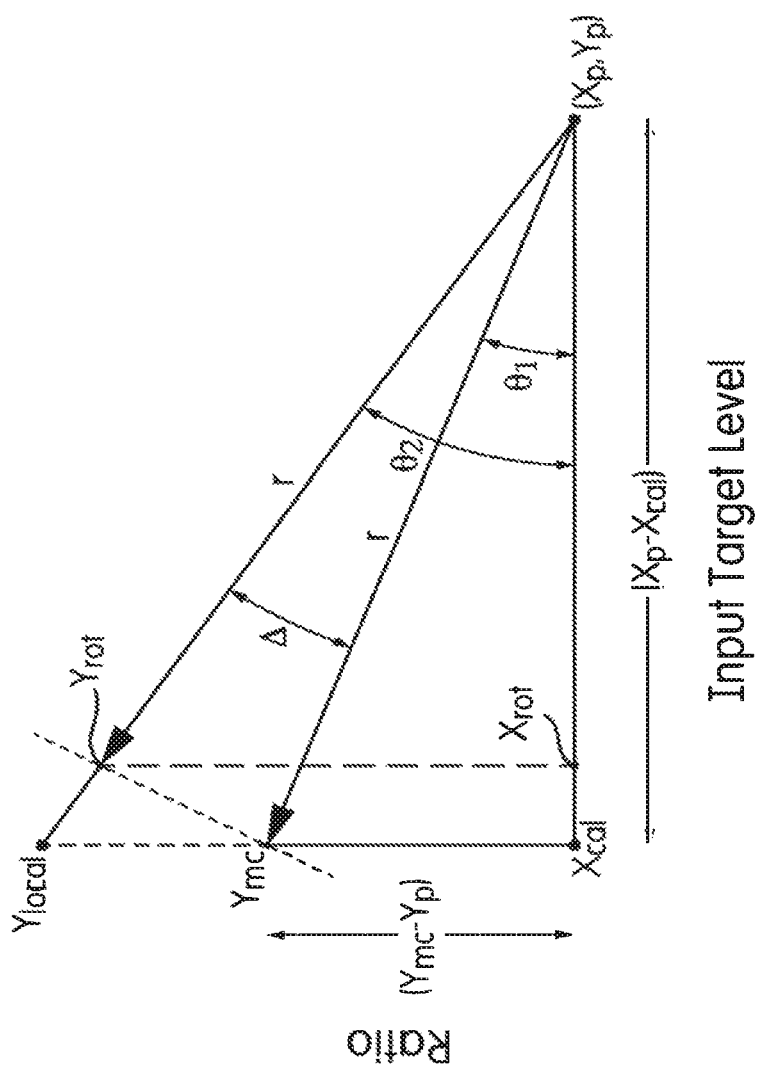
FIG. 4 is a diagram showing certain graphical features used in the rotational transformation procedure. The diagram provides the basis for transforming the data point ($X_{cal}$, $Y_{mc}$) to ($X_{rot}$, $Y_{rot}$).

A diagram showing how a master curve data point $(X_{cal}, Y_{mc})$ is rotationally transformed to $(X_{rot}, Y_{rot})$ is presented in FIG. 4. Summarized results of the rotational transformation are presented in Table 3.

TABLE 3

Rotationally Transformed Master Curve Coordinates

| Target Input (log copies/sample) | $X_{rot}$ | $Y_{rot}$ |
|---|---|---|
| 2 | 2.2033 | 2.7820 |
| 3 | 3.1554 | 2.2844 |

Figure 5:
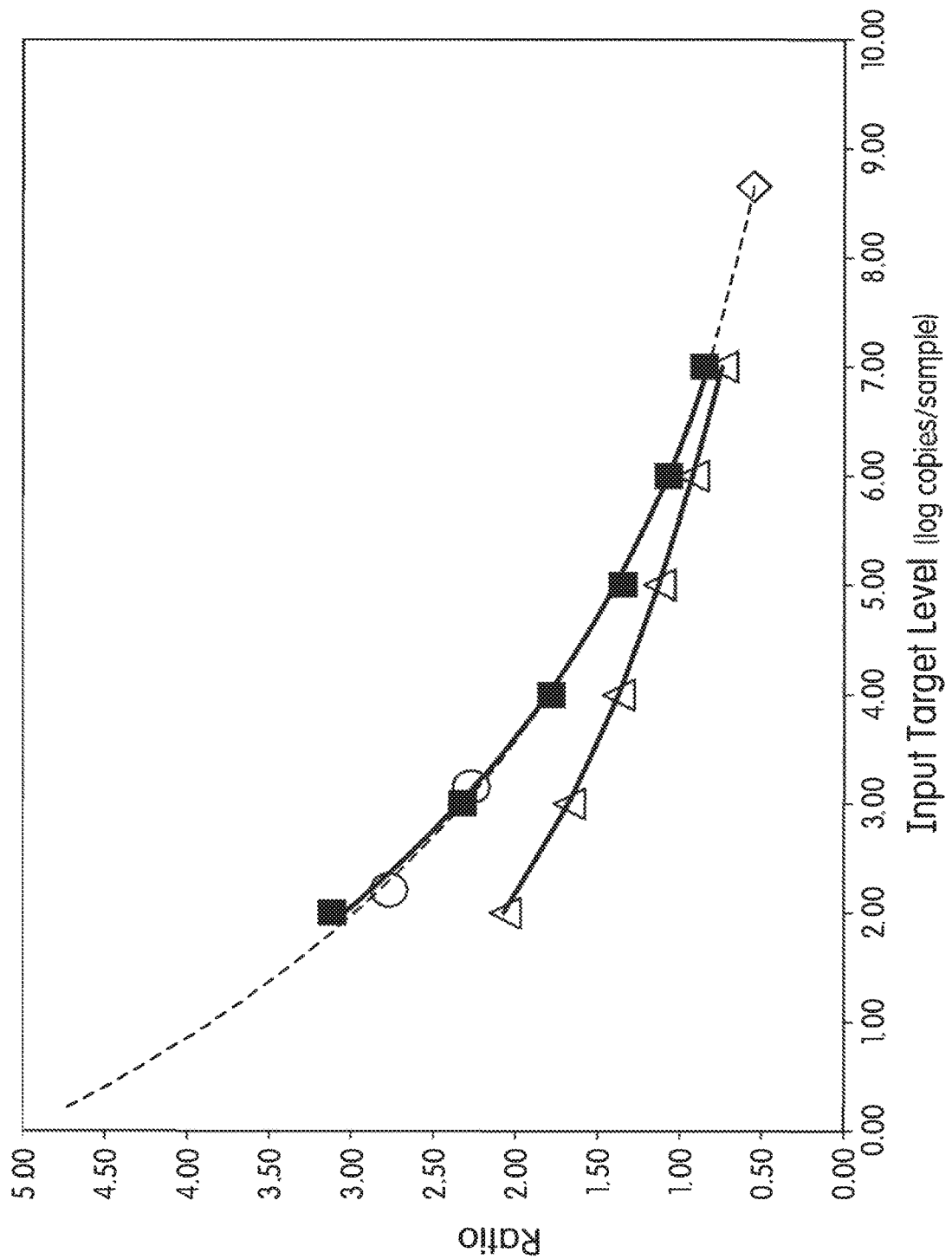
FIG. 5 is a graph having three different fitted curves. A stored master curve is shown with open triangles. A local calibration curve is shown with filled squares and a heavy black curve. A pivot point is indicated by an open diamond. Two data points representing rotational transforms from the stored master curve are indicated by open circles. A dashed curve, closely related to the local curve, is fitted to the pivot point and two rotational transforms.

FIG. 5 graphically illustrates results of the rotational transformation procedure. The fitted master curve, which is identical to the master curve shown in FIG. 1, is shown with open triangles. The fitted local calibration curve is shown with filled squares, and a heavy curve. The position of the pivot point, which corresponds to the intersection of the two fitted curves, is marked by an open diamond. The two rotational transforms from Table 3 are marked by open circles. The dashed curve in the figure is the product of exponential curve fitting the pivot point and the two rotational transforms. Significantly, the curve resulting from the rotational transformation procedure, which determined an angle of rotation using input from amplification of a single calibration standard on the local instrument, very closely matched the fitted local curve.

Quantitative results obtained using the local calibration curve (i.e., corresponding to plotted ratio values for input target levels of from $10^2$ to $10^7$ copies/sample in Table 1) and the curve including rotational transforms of the master curve were compared using fitted equations for each curve. First, the fitted equation for the local curve was used to calculate ratio values (i.e., Y-values) corresponding to specified target input amounts (i.e., using 2, 3, 4 . . . log copies/sample as X-values). Next, the resulting ratio values were substituted into the fitted equations for both the local and rotationally transformed master curves, and the results calculated. Finally, differences between the calculated target amounts were compared by subtracting one from the other. This comparative approach was appropriate because X-values of the rotationally transformed data points do not align exactly with the X-values used to generate the local curve.

The fitted equation for the rotationally transformed master curve was given by Equation 9 ($R^2$ was 0.9993).

$$Y_{rot}=5.0057e^{-0.257X} \quad \text{[Equation 9]}$$

As presented above, the fitted equation for the local calibration curve was given by Equation 2 ($R^2$ was 0.9979).

$$Y_{local}=5.1312e^{-0.26X} \quad \text{[Equation 2]}$$

Table 4 presents input target values calculated for various ratio values using the fitted local curve, and the rotationally transformed master curve. The last column shows differences between these two calculated values.

TABLE 4

Differences Between Fitted Local Curve and Rotationally Transformed Curve are Minimal

| Ratio Value ($TTime_{Target}$/$TTime_{IC}$) | Calculated Target Input (log copies) Based on Fitted Local Curve | Calculated Target Input (log copies) Based on Fitted Transformed Curve | Difference |
| --- | --- | --- | --- |
| 3.051 | 2.000 | 1.927 | −0.073 |
| 2.352 | 3.000 | 2.939 | −0.061 |
| 1.814 | 4.000 | 3.950 | −0.050 |
| 1.398 | 5.000 | 4.962 | −0.038 |
| 1.078 | 6.000 | 5.974 | −0.026 |
| 0.831 | 7.000 | 6.985 | −0.015 |

Results presented in Table 4 indicated that the local curve and the rotationally transformed master curve were closely related. Indeed, an absolute value of less than about 0.250 in the last column of Table 4 would generally be regarded as indicating excellent results. Thus, by the rotational transformation approach it was essentially possible to convert the stored master curve (i.e., that had been prepared on a first set of instruments) into the local calibration curve prepared on a different instrument by first transforming data points from the master curve, and then fitting an equation to the transformed data points and the pivot point. The angle used for executing the rotational transformation was determined using results from amplification of a single calibration standard on the local instrument, together with the pivot point.

The foregoing Example demonstrated that two calibration curves (i.e., local, and stored master or reference calibration curves) produced on different instruments were related to each other by rotation about a pivot point defined by the intersection of the two curves. Thus, the pivot point was a component of both calibration curves, and so, once determined, would be useful for preparing additional calibration curves in system re-calibration procedures on the same instrument. Moreover, reasoning that all calibration curves for a particular real-time nucleic acid amplification assay would share the pivot point in common, it followed that the pivot point could be used in combination with a result from amplification of an adjustment calibrator on a local instrument, without transformation.

The following Example shows how the data from the preceding Example was used to simulate a case wherein an end-user can: (1) prepare a calibration curve on a local instrument (e.g., using data from Table 1 corresponding to four of six of the given target input levels); (2) compare the local calibration curve with a stored master calibration curve produced on one or more different instruments (e.g., represented by Equation 1) to determine a pivot point; (3) produce an adjusted calibration curve on the local instrument using only the determined pivot point and one of the two results from Table 1 not used to prepare the local curve; and (4) use the adjusted calibration curve to determine the starting quantity of target nucleic acid present in a test sample (e.g., simulated by the remaining calibrator from Table 1, also not used to prepare the local curve). In another preferred embodiment, the reference curve is prepared using the local instrument, as illustrated in subsequent Examples.

Example 2 illustrates a system re-calibration procedure wherein a pivot point was determined using one data set from a local instrument, and subsequently used in combination with a result obtained for a single adjustment calibrator on the local instrument to quantify a simulated test sample. Note that value-assigned quantities for input target levels were used for the simulated adjustment calibrator, and the simulated test sample. This illustrates a single-point system re-calibration procedure.

Example 2

Establishing and Using a Pivot Point on a Local Instrument

System re-calibration was simulated using the same calibration data from Table 1 that was used in Example 1. Curve fitting of the data in column 2 of Table 1, for target input levels of from $10^2$ to $10^7$ copies/sample, yielded a stored master calibration curve defined by Equation 1. Again, these internal calibration results were obtained using three instruments other than the end-user's local instrument, and conveniently could be provided to the end-user by a kit manufacturer in the form of a bar coded equation, or coefficients therefor. A simulated local calibration curve was prepared by curve fitting data from column 3 of Table 1 corresponding to target input levels of $10^2$, $10^4$, $10^6$ and $10^7$ copies/sample. These values represent internal calibration data that might be obtained by an end-user upon performing an initial calibration procedure the first time a kit is used on the local instrument. The resulting, fitted local calibration curve (i.e., an "initial" calibration curve) was given by Equation 10 ($R^2$ was 0.9987). The local instrument programmed with this calibration curve could be used immediately for quantifying target nucleic acid present in test samples.

$$Y_{local} = 5.1849e^{-0.261X} \quad \text{[Equation 10]}$$

Setting Equation 1 and Equation 10 equal to each other permitted identification of the point of identity (i.e., the pivot point), which had the coordinates: (8.6992, 0.5354). The pivot point is not required for use of the initial calibration curve in procedures for quantifying analyte nucleic acid in test samples, but can be stored for future re-calibration procedures.

At a future point in time the end-user desires to re-calibrate the local instrument to quantify analyte nucleic acid contained in a new test sample. To model a single-point system re-calibration procedure, the data point from Table 1 corresponding to the input target level of $10^3$ copies/sample (value-assigned as 3.0305 log copies/sample) served as a simulated adjustment calibrator. Thus, the single data point (3.0305, 2.3336) and the pivot point described in the preceding paragraph were used in combination for exponential curve fitting. The resulting, adjusted calibration curve was defined by Equation 11 ($R^2$ was 1.00).

$$Y_{1\text{-}pt\, re\text{-}cal} = 5.1265e^{-0.26X} \quad \text{[Equation 11]}$$

Figure 6:
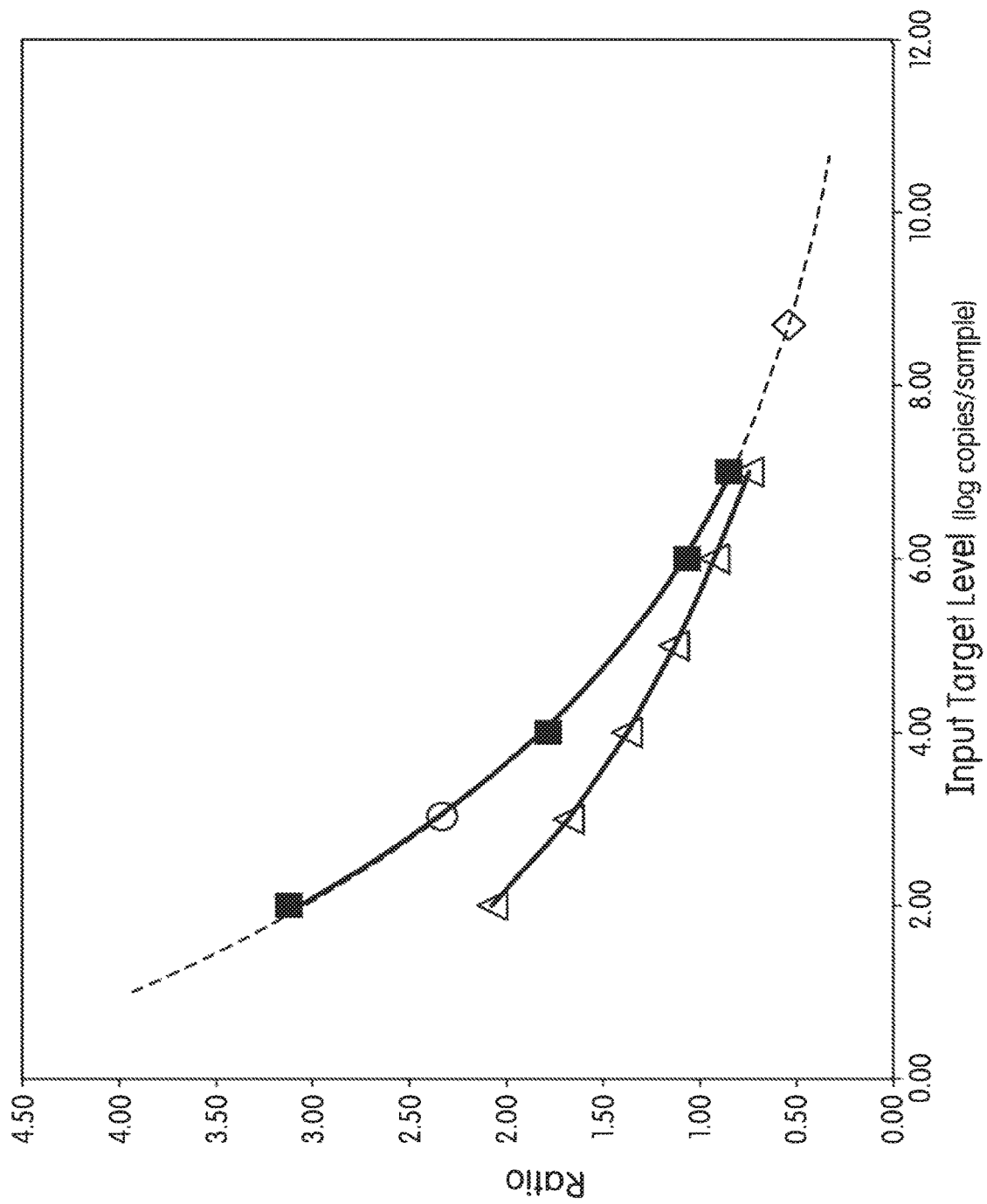
FIG. 6 is a graph having three different fitted curves. A stored master curve is shown with open triangles. A local calibration curve fitted to four data points is shown with filled squares and a heavy black curve. A pivot point is indicated by an open diamond. A data point representing the ratio value determined on the local instrument using a single adjustment calibrator is indicated by an open circle. A dashed curve closely related to the local curve, and fitted to the pivot point and data point for the single adjustment calibrator, was used for quantifying a simulated test sample having an input target level of about $10^5$ copies/sample.

FIG. 6 graphically illustrates results of the single-point re-calibration procedure. The fitted master calibration curve is shown with open triangles. The fitted initial calibration curve generated on the local instrument using the indicated four data points is shown with filled squares, and a heavy curve. The position of the pivot point, which corresponds to the intersection of the fitted master curve and the initial calibration curve, is marked by an open diamond. The data point corresponding to the simulated adjustment calibrator result (i.e., without rotational transformation) is indicated by the open circle. The dashed curve is the exponential fit using the pivot point and the single adjustment calibrator data points. The close relationship between initial calibration curve and the dashed curve resulting from the re-calibration procedure confirmed that the pivot point could be used in combination with the normalized result from a single adjustment calibrator to yield good results.

The end-user next desires to use the local instrument, programmed to use the adjusted calibration curve defined by Equation 11, for quantifying analyte nucleic acid present in a test sample. The ratio value from Table 1 corresponding to the input target copy level $10^5$ copies/sample (value-assigned as 5.122 log copies/sample) was used to simulate the test sample result to be used for quantifying analyte nucleic acid. Substituting this ratio value (i.e., 1.3549) into Equation 11 and then solving for the corresponding starting amount of target nucleic acid (i.e., "X") gave 5.118 log copies/sample. This calculated result was lower than the actual, value-assigned target copy level by only 0.004 log copies/sample. Thus, given the identity of a pivot point and the result from amplifying a single adjustment calibrator on the local instrument, it was possible to approximate a complete local calibration curve very accurately. In this instance, the calibration curve was a non-linear calibration curve, and was used for quantifying a simulated test sample.

The following Example illustrates how a pivot point, identified by the intersection of two linear calibration plots, was used for approximating linear calibration plots on a local instrument. The Example also illustrates how the pivot point can be identified using a first instrument or set of instruments (e.g., representing instruments controlled by the manufacturer of nucleic acid assay kits), and then used on a different instrument (e.g., representing an end-user's "local" instrument). As in the preceding Examples, rotational transformation of one or more data points from a stored reference curve (e.g., one of the curves used for identifying the pivot point) was used to create a complete calibration curve on the local instrument.

Nucleic acid target capture and amplification procedures in all of the following Examples were performed at Gen-Probe Incorporated (San Diego, Calif.) using an automated instrument capable of amplifying nucleic acids under temperature-controlled conditions, and monitoring amplicon production (e.g., by optical monitoring of fluorescence) as a function of cycle number or time. Published U.S. Patent Application 2011/0147610, the entire disclosure of which is incorporated by reference herein, details features of a preferred instrument for performing real-time amplification procedures. Another preferred instrument is described in U.S. Pat. No. 6,713,297, the disclosure of which is incorporated by reference herein. Synthetic transcripts for analyte target and IC served as templates in the reactions. Samples to be processed and amplified were prepared by combining a constant 150,000 copies of synthetic IC transcript, and a 0.5 ml aliquot containing an amount of an analyte target transcript that served as a template for amplification. Concentration of the target nucleic acid used in the procedure ranged from $10^2$ to $10^7$ copies/ml across sets of six reactions. Amplification reactions were carried out using template nucleic acids following target-capture and wash steps to remove or reduce impurities in the samples. Target and IC templates were coamplified in the same reaction using independent primer sets (i.e., no shared primers). Amplification products were detected and monitored using distinguishably labeled, amplicon-specific molecular torch hybridization probes, each harboring a different fluorescent reporter. All amplification reactions were performed in replicates. Threshold time values representing indicia of amplification for each of the coamplified target and IC were determined using the TTime algorithm, essentially as described in published U.S. Patent Application No. 2006/0276972, the disclosure of which is incorporated by reference herein. Ratio values were calculated by dividing the TTime value determined for target by the TTime value determined for IC that amplified in the same reaction.

Example 3 describes how a linear reference calibration plot (e.g., a stored reference plot, or master curve) that includes a pivot-point can be adjusted by rotation about the pivot-point through an angle determined by results from amplifying only a single adjustment calibrator on a local instrument. The pivot-point was identified using fitted linear calibration plots generated on instruments identified as "V47" and "V35" (e.g., first and second instruments). The pivot-point, together with a single data point from the fitted calibration plot generated on instrument V47, and a single normalized ratio result generated on a third instrument ("V53"), representing an end-user's local instrument, approximated a complete local calibration plot by a process that included rotational transformation. Results proved that rotational transformation of data points from one linear calibration plot (e.g., a stored reference plot) yielded an adjusted calibration plot useful for quantifying target samples on a local instrument. Results further demonstrated how the pivot point and a result from amplification of only a single adjustment calibrator on the local instrument could be used to prepare a useful calibration plot, even when the pivot point was determined by results obtained on different real-time amplification instruments.

Example 3

Internal Calibration Adjustment on a Local Instrument by Rotational Transformation of One of More Points from a Stored Reference Curve Six nucleic acid calibration standards were amplified using a first real-time instrument identified as V47. All reactions on instrument V47 were carried out using a target capture reagent ("TCR") that had been subjected to heating at 55° C. for 14 days to promote accelerated degradation. Samples used for calibration reactions had volumes of 0.5 ml each, and nucleic acid target concentrations that ranged from $10^2$ to $10^7$ copies/ml. Nucleic acids captured from the different samples were coamplified with a fixed 150,000 copies of IC in replicates. Measured TTime indicia of amplification for target and IC were normalized to yield threshold ratio values (i.e., $TTime_{Target}/TTime_{IC}$). A linear calibration plot of the ratio values as a function of input target quantity (e.g., concentration) was established and used for assigning actual target starting quantities, referred to herein as "value-assigned" quantities, to each different calibration standard. Table 5 presents summarized results and value-assigned concentrations of the calibration standards, where value assignments were established using all six calibrators.

TABLE 5

Summarized Results for Calibration Standards Amplified on Instrument V47

| Cal. No. | Target Quantity (log copies/ml) | Value-Assigned Target Quantity (log copies/ml) | Ratio ($TTime_{Target}/TTime_{IC}$) |
|---|---|---|---|
| 1 | 2.00 | 2.0674 | 0.9773 |
| 2 | 3.00 | 2.9535 | 0.8709 |
| 3 | 4.00 | 3.9629 | 0.7496 |
| 4 | 5.00 | 4.9648 | 0.6292 |
| 5 | 6.00 | 6.0308 | 0.5012 |
| 6 | 7.00 | 7.0206 | 0.3823 |

The fitted linear calibration plot established using the data from instrument V47 (e.g., representing a first calibration reference curve) was defined by Equation 12, wherein X and Y are the target quantity (e.g., concentration) and ratio values, respectively.

$$Y=-0.1201X+1.2257 \qquad \text{[Equation 12]}$$

Nucleic acid amplification reactions similar to those described in the preceding paragraph, except that heat-treated TCR was substituted by standard TCR that had not been subjected to accelerated degradation, were performed and monitored on a second real-time instrument identified as V35. Table 6 presents summarized results and value-assigned concentrations of the calibration standards, where value assignments were made using all six calibrators.

TABLE 6

Summarized Results for Calibration Standards Amplified on Instrument V35

| Cal. No. | Target Quantity (log copies/ml) | Value-Assigned Target Quantity (log copies/ml) | Ratio ($TTime_{Target}/TTime_{IC}$) |
|---|---|---|---|
| 1 | 2.00 | 2.0495 | 1.0582 |
| 2 | 3.00 | 2.9625 | 0.9425 |
| 3 | 4.00 | 3.9608 | 0.8159 |
| 4 | 5.00 | 4.9985 | 0.6844 |
| 5 | 6.00 | 6.0230 | 0.5546 |
| 6 | 7.00 | 7.0056 | 0.4301 |

The fitted linear calibration plot established using the data from instrument V35 (e.g., representing a second calibration reference curve) was defined by Equation 13, wherein X and Y are the target quantity (e.g., concentration) and ratio values, respectively.

$$Y=-0.1267X+1.3179 \qquad \text{[Equation 13]}$$

The rotational transformation procedure was performed using information from Tables 5 and 6. First, intersection of the two linear plots by simultaneously solving Equations 12 and 13 identified the following pivot point: (14.0372, −0.4606). Note that rounding errors lead to slight discrepancies between the presented and calculated values, but that these slight differences do not alter the usefulness of the procedure. Fitted Equation 12 was arbitrarily selected and solved to determine the ratio value corresponding to an input calibration standard of $10^3$ copies/ml. The resulting data point falling on the fitted linear reference plot had the coordinates (3, 0.8653), and was subsequently used for demonstrating rotational transformation of a single point from the reference curve. Notably, selection of the $10^3$ copies/ml target level data point was also an arbitrary choice.

Single-point calibration on a local instrument was demonstrated next. Reactions carried out using standard TCR and amplification procedures on a simulated local instrument identified as "V53." In this illustration the local instrument was not among the set used for establishing the fixed-point. All reactions included the same constant amount of IC as the reactions used for determining the two reference curves and the fixed-point, and variable amounts of analyte target nucleic acid corresponding to the six calibration standards. TTime values determined for the target and IC in each reaction were used for calculating ratios. Starting target nucleic acid concentrations ranged from $10^2$ to $10^7$ copies/ml across the six reactions. Summarized results for amplification reactions performed on instrument V53, including value assignments made using all six calibrators, are presented in Table 7.

TABLE 7

Summarized Results for Calibration Standards Amplified on Instrument V53

| Cal. No. | Target Quantity (log copies/ml) | Value-Assigned Target Quantity (log copies/ml) | Ratio ($TTime_{Target}/TTime_{IC}$) |
|---|---|---|---|
| 1 | 2.00 | 2.0248 | 1.0418 |
| 2 | 3.00 | 3.0321 | 0.9173 |
| 3 | 4.00 | 3.9131 | 0.8084 |
| 4 | 5.00 | 4.9973 | 0.6744 |
| 5 | 6.00 | 6.0135 | 0.5488 |
| 6 | 7.00 | 7.0191 | 0.4245 |

The value-assigned target quantity and ratio determined for the second calibration standard (i.e., Cal. No. 2) in Table 7 and the pivot point were used for establishing two linear calibration plots that were compared with each other. One of the plots resulted from combined use of the pivot point and the rotational transform of the above-described single data point from the arbitrarily selected first reference plot. The other plot resulted from rotational transformation of a plurality of data points from that reference plot. Results from the remaining calibration standards among those processed on instrument V53 served as simulated unknowns that were quantified using the two linear calibration plots, each having been established using the result from the single adjustment calibrator amplified on the local instrument.

The above-described single data point from the reference curve (i.e., (3, 0.8653)) was rotationally transformed using results from amplification of the Cal. No. 2 simulated adjustment calibrator on the local instrument (i.e., V53) to determine the angle of rotation about the pivot point (14.0372, −0.4606) essentially as follows. In this description reference is made to FIG. 7. Data points used in the calculations were as follows.

$(X_{pivot}, Y_{pivot}) = (14.0372, -0.4606)$

The reference data point to be rotationally transformed had the following coordinates.

$(X_{ref}, Y_{ref}) = (3, 0.8653)$

The model single-point adjustment calibration standard (i.e., Cal. No. 2 from Table 7) to be used for determining the angle of rotation had the following coordinates.

$(X_{cal}, Y_{local}) = (3.0321, 0.9173)$

Figure 7:
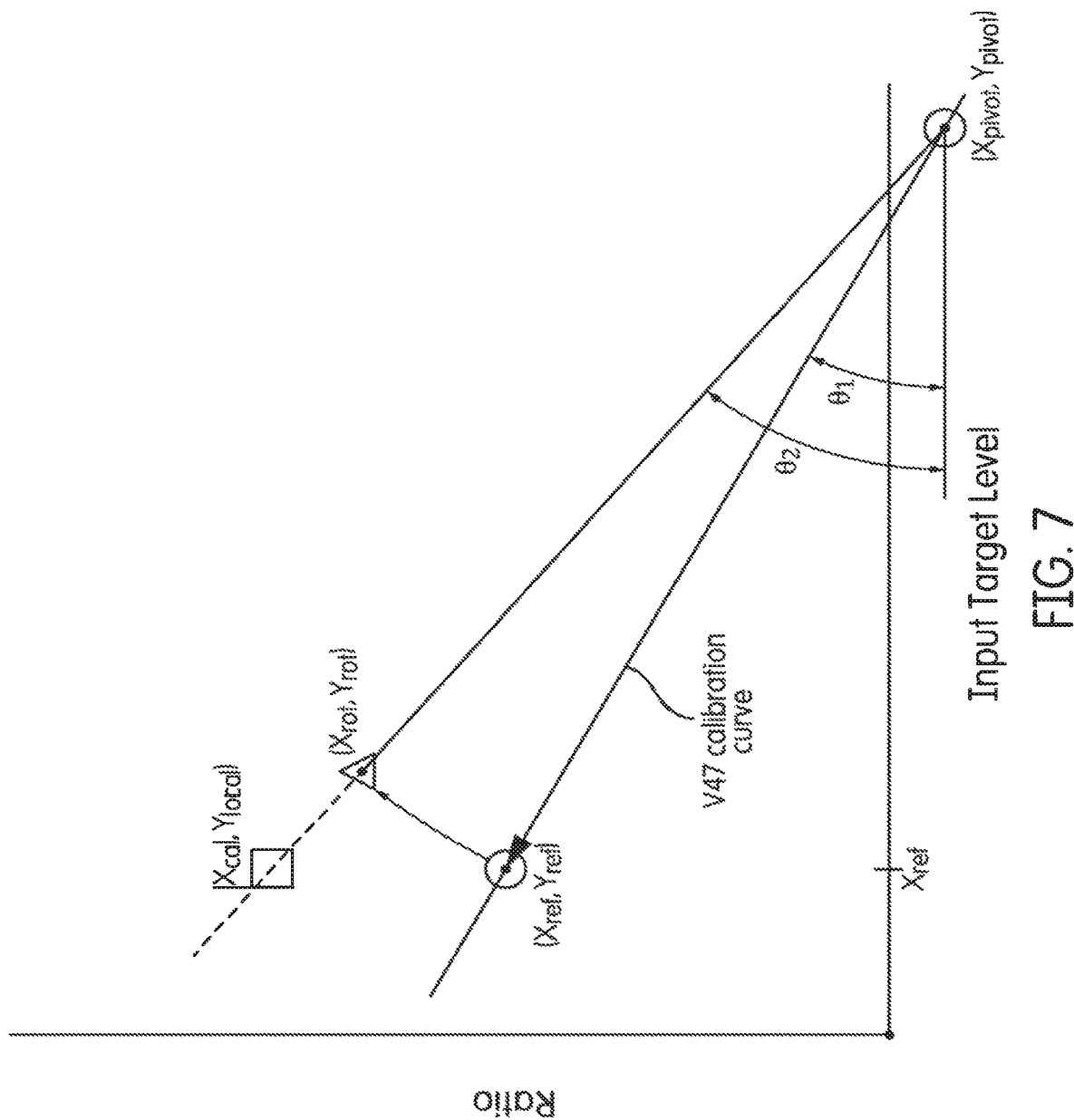
FIG. 7 is a diagram illustrating the rotational transformation procedure for linear calibration plots. The pivot point is identified by coordinates $(X_{pivot}, Y_{pivot})$. The adjustment calibration standard data point determined by amplification and monitoring with the local instrument is identified by $(X_{cal}, Y_{local})$. The reference curve data point to be rotated is identified by $(X_{ref}, Y_{ref})$. The rotational transform of this latter data point is identified by $(X_{rot}, Y_{rot})$. In preferred approaches, the reference curve data point has the same X-value as the adjustment calibration standard (i.e., $X_{ref}=X_{cal}$) used for determining the angle of rotation. This case is illustrated in the diagram.

Referring still to FIG. 7, the angle (i.e., $\theta_1$) between the horizontal axis and a vector extending from the pivot point to the coordinates of the reference curve data point to be transformed was calculated using the following relationship.

$\text{Tan } \theta_1 = (Y_{ref} - Y_{pivot})/(X_{pivot} - X_{ref})$ [Equation 14]

$\text{Tan } \theta_1 = 0.1201$ $\theta_1 = 0.1196$ radians

Referring still to FIG. 7, the magnitude (i.e., r) of the vector having its origin at the pivot point $(X_{pivot}, Y_{pivot})$, and terminating at the coordinates of the reference data point on the fitted reference plot $(X_{ref}, Y_{ref})$ was calculated as follows.

$r = (Y_{ref} - Y_{pivot})/\text{Sin } \theta_1$ [Equation 15]

$r = 11.1166$

Referring still to FIG. 7, the angle (i.e., $\theta_2$) between the horizontal axis and a ray extending from the pivot point through the coordinates for the adjustment calibrator amplified on the local instrument was calculated using the following relationship.

$\text{Tan } \theta_2 = (Y_{local} - Y_{pivot})/(X_{pivot} - X_{cal})$ [Equation 16]

$\text{Tan } \theta_2 = 0.1252$ $\theta_2 = 0.1246$ radians

Referring still to FIG. 7, the difference between $\theta_2$ and $\theta_1$ was determined as follows.

$\Delta = \theta_2 - \theta_1$ [Equation 17]

$\Delta = 0.0050$ radians

The coordinates for the rotationally transformed reference data point were calculated as follows.

$X_{rot} = X_{pivot} - r \cos(\theta_1 + \Delta)$ [Equation 18]

$X_{rot} = 3.0068$ $Y_{rot} = Y_{pivot} + r \sin(\theta_1 + \Delta)$ [Equation 19]

$Y_{rot} = 0.9205$

A two-point linear calibration plot that included the pivot point (i.e., (14.0372, −0.4606)) and the rotationally transformed reference data point (i.e., (3.0068, 0.9205)) was defined by the following equation.

$Y = -0.1252X + 1.2969$ [Equation 20]

Using the ratio values from Table 7 (i.e., "Y" in Equation 20), it was possible to calculate starting target concentrations (i.e., "X" in Equation 20). Treating calibration standards 1 and 3-6 as unknowns to be quantified, it was possible to compare calculated values with actual, value-assigned quantities shown in Table 7. Summarized results are presented in Table 8, with differences between calculated and actual target concentrations being presented in the last column.

TABLE 8

Internal Calibration Adjustment by Rotational Transformation of a Stored Reference Point

| Cal. No. | Value Assigned Target Quantity (log copies/ml) | Ratio ($\text{TTime}_{Target}/\text{TTime}_{IC}$) | Calculated Target Conc. (log copies/ml) | Difference (log copies/ml) |
|---|---|---|---|---|
| 1 | 2.0248 | 1.0418 | 2.0377 | 0.013 |
| 2 | 3.0321 | 0.9173 | 3.0321 | 0.000 |
| 3 | 3.9131 | 0.8084 | 3.9019 | −0.011 |
| 4 | 4.9973 | 0.6744 | 4.9721 | −0.025 |
| 5 | 6.0135 | 0.5488 | 5.9753 | −0.038 |
| 6 | 7.0191 | 0.4245 | 6.9681 | −0.051 |

Results presented in Table 8 confirmed that rotational transformation of only one stored reference point about a pivot point, by an angle determined using a single adjustment calibrator on a local instrument, was sufficient to establish a useful calibration plot when used in combination with the pivot point. Again, an absolute value of less than about 0.250 in the last column of the table would generally be regarded as indicating excellent results. Significantly, rotational transformation of the six data points in Table 5 (i.e., the stored reference curve) about the pivot point by the angle determined using the single Cal. No. 2 result obtained using the local instrument (see Table 7), and then fitting a line to the set of transformed data points (i.e., not including the pivot point) yielded an equation identical to the equation defining the line resulting from the combination of the single rotationally transformed Cal. No. 2 data point and the pivot point. Thus, rotational transformation of one or more points from a stored reference curve about a pivot point by an angle determined using a single adjustment calibrator on a local instrument created a calibration curve useful for quantifying target nucleic acid in test samples.

Since results from the foregoing procedure confirmed that useful calibration curves included the pivot point, and since a local calibration curve (e.g., prepared using all data points from Table 7) represented the gold standard for quantifying target nucleic acid on the local instrument, it followed that a useful calibration curve could be prepared using the pivot point and results from only a single adjustment calibrator run on the local instrument. In fact, testing using the pivot point and the value-assigned target quantity and ratio value from Cal. No. 2 amplified on the local instrument (see Table 7) demonstrated this to be the case.

Linear equations representing alternative calibration plots were prepared using the results described in the present Example, and then compared with each other. The calibration plots were: (1) the stored reference curve prepared using six data points from Table 5; (2) the full local curve prepared using six data points from Table 7; (3) the linear plot determined by the pivot point and the single rotationally transformed point from the reference plot; (4) the linear plot determined by rotational transformation of six data points for the reference plot (i.e., not including the pivot point); and (5) the linear plot determined by the pivot point and the result from a single adjustment calibrator (Cal. No. 2) run on the local instrument. Calculated slope and y-intercept values for the various calibration plots are presented in Table 9.

TABLE 9

Comparing Features of Alternative Linear Calibration Plots

| Linear Equation | Slope | Y-Intercept |
|---|---|---|
| Stored Reference | −0.1201 | 1.2257 |
| Local (gold standard) | −0.1236 | 1.2921 |
| Single PT MC rotated & pivot | −0.1252 | 1.2969 |
| Full MC Rotation (no pivot) | −0.1252 | 1.2969 |
| Single PT (local 10e3 & Pivot) | −0.1252 | 1.2969 |

Comparison of the slope and y-intercept values presented in Table 9 indicated that calibration plots resulting from rotational transformation of one or more data points from a stored reference plot, and the result of using the pivot point and a single adjustment calibrator run on the local instrument gave identical results. All three of these results (i.e., entries 3-5 in Table 9) were very close to slope and y-intercept values of the full calibration curve generated on the local instrument (i.e., entry 2 in Table 9). Thus, in addition to rotational calibration of one or more points from the reference curve about the pivot point by an angle determined using a result from a single adjustment calibrator run on the local instrument, a useful calibration curve was prepared by fitting a line to the pivot point and the result from a single adjustment calibrator run on the local instrument.

The foregoing Example demonstrated how dual reference calibration plots could be used to identify a pivot point, and further demonstrated how multiple useful calibration plots substantially shared the same pivot point. This established the utility of the dual reference calibration plots, even when the reference plots were determined by amplification of calibration standards on different instruments, and even when information from the reference plots was used for quantifying target nucleic acids across a broad dynamic range using results from only a single adjustment calibrator amplified on yet a different instrument (i.e., the local instrument).

The following Example illustrates yet another approach for approximating a full local calibration plot using only a single adjustment calibrator, where the approach also relies on the use of dual reference plots. Although one or both of the reference plots can be generated using results from amplification reactions performed on the local instrument to be used for quantifying test samples, the Example illustrates a more stringent case wherein three different instruments were used. As in the preceding Example, real-time amplification results from the V47 and V35 instruments were used to prepare the reference plots, and the V53 instrument served as the local instrument. The approach approximates a complete local calibration plot from a single adjustment calibrator data point by requiring, at all points along the approximated local plot, a constant proportionality relationship to the result of a mathematical function that relates the reference curves to each other. In the context of the invention, the mathematical function can involve an operation that includes any of addition, subtraction, multiplication or division. The process of subtraction to result in a difference between the two reference curves as a function of starting target quantity (e.g., concentration) is presently preferred, although each of the other operations has been tested and shown to work.

Good results have been achieved by specifying constant proportionality between: (a) the difference between the ratio value determined for an adjustment calibrator and one of the two reference curves at the value-assigned target quantity of the calibrator; and (b) the difference between the two reference curves at that value-assigned target quantity of the adjustment calibrator. In this instance, the reference curves were related to each other as a function of starting target quantity (e.g., concentration) by a process involving subtraction. As indicated below, this approach and those described in Example 3 (i.e., that relied on calculation and use of the pivot point) yielded identical results.

Example 4

Approximating a Complete Local Calibration Curve Using Results from a Single Adjustment Calibrator and Two Stored Reference Curves Equation 12, based on results from amplification of calibration standards using instrument V47, was used to describe a first calibration reference curve (Reference Curve 1), and Equation 13, based on results from amplification of calibration standards on instrument V35, was used to describe a second calibration reference curve (Reference Curve 2). The result for the second calibration standard (Cal. No. 2) in Table 7 served as a simulated single point adjustment calibrator amplified on local instrument V53. Remaining entries in Table 7 served as simulated test samples to be quantified on the local instrument using a full calibration curve prepared using the Cal. No. 2 result.

Figure 8:
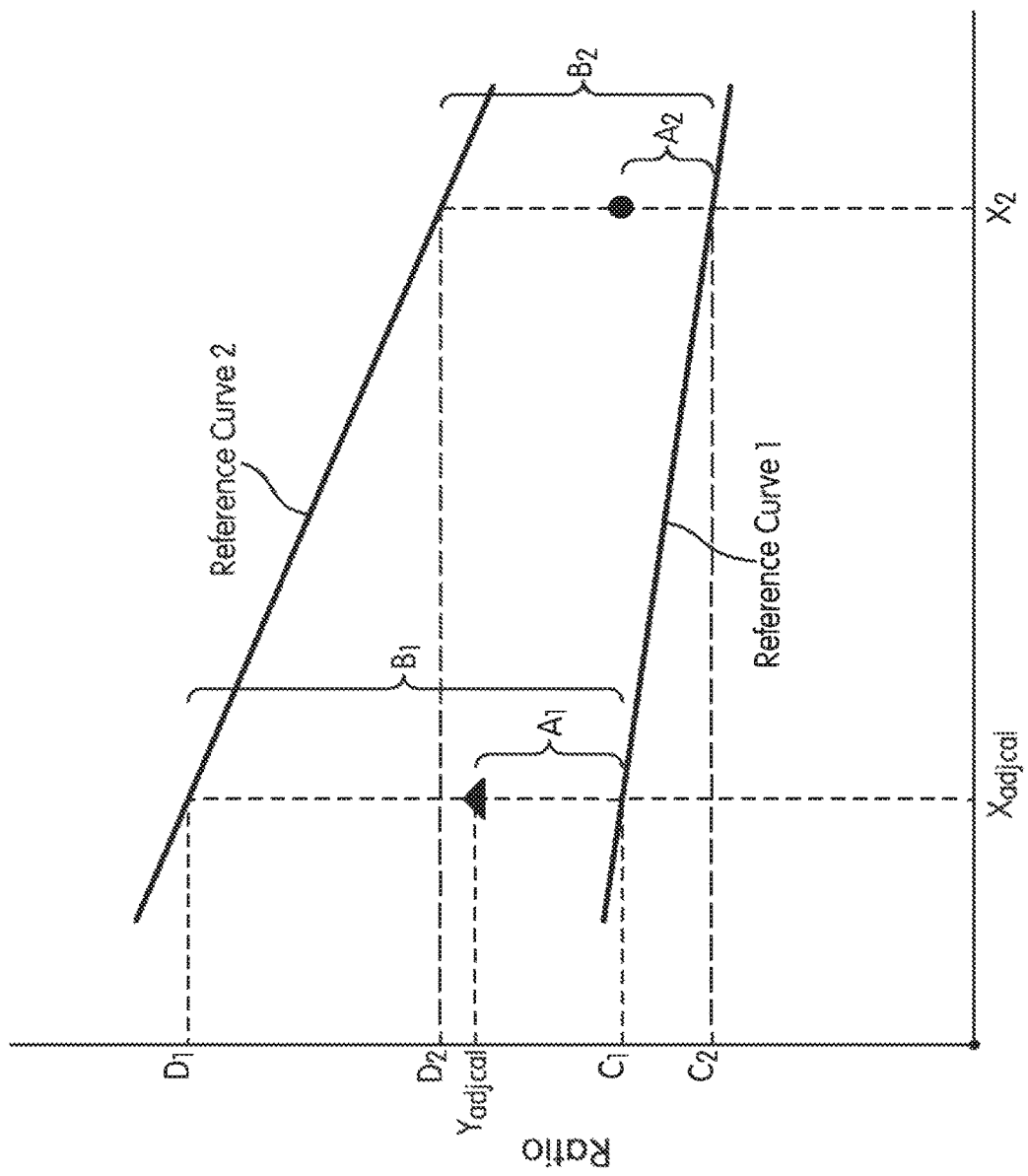
FIG. 8 is a diagram illustrating how dual reference curves, together with results from a single adjustment calibrator (filled triangle), can be used to establish a second point (filled circle) to be used for curve fitting to approximate a complete local calibration plot.

The procedure used for approximating a local calibration curve using a single adjustment calibrator and two reference curves can be understood with reference to FIG. 8. Fitted equations for the two reference curves were each solved at input target levels corresponding to the known quantity of target present in the adjustment calibrator (i.e., $X_{adj\ cal}$) to determine ratio values (i.e., $C_1$ and $D_1$), and the difference between these determined ratio values was calculated (i.e., $B_1$). The difference between the ratio value (i.e., y-value) of the adjustment calibrator (i.e., $Y_{adj\ cal}$) determined on the local instrument and an arbitrarily selected one of the reference curves (e.g., Reference Curve 1) was next determined (this difference being shown as $A_1$). Relative to the difference between the two reference curves (i.e., $B_1$) at the input target level of the adjustment calibrator, the fraction represented by the difference (i.e., $A_1$) between the y-value of the adjustment calibrator determined on the local instrument and the arbitrarily selected one of the reference curves was represented $A_1/B_1$. It was this proportional relationship that was to be maintained constant at all points along the approximated local plot that was to be created. Multiplying $A_1/B_1$ by the value of $B_1$ gave the value of $A_1$. Thus, the y-value coordinate (i.e., the ratio value) for the adjustment calibrator was given by the following equation.

$$Y_{adj\ cal} = [C1 + (A_1/B_1)(B_1)] \quad \text{[Equation 21]}$$

The fitted equations for the two reference curves were next solved to determine ratio values at an arbitrarily selected input target level (i.e., $X_2$) to be used for establishing a second data point in a two-point linear calibration plot. Solutions to the first and second fitted equations at this input target level are shown in FIG. 8 as $C_2$ and $D_2$, respectively. In this illustration, the two fitted equations were solved for an arbitrarily selected target input level of $10^7$ copies/ml, which corresponded to the high calibrator in Table 7. Since the difference (i.e., $A_2$) between the y-value of the approximated local calibration curve and the reference curve selected for comparison therewith (Reference Curve 1) is maintained at a constant proportion or fraction of the difference between the two reference curves (i.e., $B_2$) across the dynamic range of the assay, it follows that the y-value of the approximated local calibration curve at arbitrary "target level 2" will be given by the following equation.

$$Y_{local\ at\ target\ level\ 2} = [C_2 + (A_1/B_1)(B_2)] \quad \text{[Equation 22]}$$

The approximated local calibration curve, based on the single adjustment calibrator result and information about the two reference curves, was defined by a linear plot that included the following two data points. First was the value-assigned target level (e.g., $X_{adj\ cal}$) and the determined ratio value result (e.g., $Y_{adj\ cal}$) of the adjustment calibrator. Second was the arbitrarily selected input target level (e.g., "$X_2$"), and the calculated ratio value in accordance with Equation 22 (e.g., $Y_{local\ at\ target\ level\ 2}$). Basis for the numerical values associated with the two data points follows.

Reference Curve 1 equation:

$$y = -0.1201x + 1.2257 \quad \text{[Equation 12]}$$

Reference Curve 2 equation:

$$y = -0.1267x + 1.3179 \quad \text{[Equation 13]}$$

Adjustment calibrator (3.0321, 0.9173)

Calculated values associated with calibration curves at the target input level of the adjustment calibrator:

$C_1 = 0.8615$
$D_1 = 0.9337$
$B_1 = 0.0722$
$A_1 = 0.0558$

Calculated values associated with calibration curves at an arbitrary input target level of $10^7$ copies/ml.

$C_2 = 0.3850$
$D_2 = 0.4310$
$B_2 = 0.0460$
$A_2 = 0.0355$

Based on these measured and calculated values, the two points used for establishing the linear, local calibration plot by single-point, dual reference calibration adjustment were: (3.0321, 0.9173) and (7, 0.4205). The equation for the linear plot was as follows.

$$y = -0.1252x + 1.2969 \quad \text{[Equation 23]}$$

Using the ratio values from Table 7 (i.e., "Y" in Equation 23), it was possible to calculate starting target concentrations (i.e., "X" in Equation 23). Treating calibration standards 1 and 3-6 as unknowns to be quantified, it was possible to compare calculated values with actual, value-assigned quantities shown in Table 7. Summarized results are presented in Table 10, with differences between calculated and actual target concentrations being presented in the last column.

TABLE 10

Quantitation of Test Samples Using Single-Point, Dual Reference Calibration Adjustment

| Cal. No. | Value Assigned Target Quantity (log copies/ml) | Ratio ($TTime_{Target}/TTime_{IC}$) | Calculated Target Quantity (log copies/ml) | Difference (log copies/ml) |
|---|---|---|---|---|
| 1 | 2.0248 | 1.0418 | 2.0377 | 0.013 |
| 2 | 3.0321 | 0.9173 | 3.0321 | 0.000 |
| 3 | 3.9131 | 0.8084 | 3.9019 | −0.011 |
| 4 | 4.9973 | 0.6744 | 4.9722 | −0.025 |
| 5 | 6.0135 | 0.5488 | 5.9754 | −0.038 |
| 6 | 7.0191 | 0.4245 | 6.9683 | −0.051 |

It will be clear from inspection of the last columns in Tables 8 and 10, and by comparison of Equation 23 and the slope and y-intercept values appearing in Table 9 that identical results were achieved by: (1) specifying a calibration curve using the pivot point and a single point from the reference plot following rotational transformation by an angle determined using a single adjustment calibrator run on the local instrument; (2) specifying a calibration curve by rotational transformation of a plurality of points from the reference plot, where the points are rotated about the pivot point by an angle determined using a single adjustment calibrator run on the local instrument; (3) specifying a calibration curve using the pivot point and a single point corresponding to the adjustment calibrator run on the local instrument; and (4) specifying a calibration curve using a single data point corresponding to the adjustment calibrator amplified on the local instrument, and by maintaining a constant proportionality relationship relative to the two fitted reference plots.

This invention has been described with reference to a number of specific examples and embodiments thereof. Of course, a number of different embodiments of the present invention will suggest themselves to those having ordinary skill in the art upon review of the foregoing detailed description. Thus, the true scope of the present invention is to be determined upon reference to the appended claims.

What is claimed is:

1. A method of calibrating a local instrument that performs a quantitative nucleic acid amplification assay, the method comprising the steps of:
   (a) causing an electronic spreadsheet to comprise coefficients of fitted equations for each of a first calibration curve and a second calibration curve,
      wherein each of the curves relates indicia of amplification for a plurality of analyte polynucleotide standards normalized to indicia of amplification for a fixed amount of an internal calibrator that co-amplified therewith as a function of starting amounts of the analyte polynucleotide in amplification reactions of the quantitative nucleic acid amplification assay, and
      wherein the first and second calibration curves are different from each other;
   (b) obtaining an adjustment calibrator comprising a known amount of the analyte polynucleotide and the fixed amount of the internal calibrator;
   (c) co-amplifying, in a real-time amplification reaction performed with the local instrument, the analyte polynucleotide and the internal calibrator of the adjustment calibrator, whereby indicia of amplification for each of the analyte polynucleotide and the internal calibrator of the adjustment calibrator are determined; and (d) establishing a local calibration curve using the electronic spreadsheet from step (a) and each of the indicia of amplification determined in step (c), wherein the local calibration curve specifies values for indicia of amplification for the analyte polynucleotide normalized to indicia of amplification for the internal calibrator as a function of starting amounts of the analyte polynucleotide, and wherein the local calibration curve is electronically stored in a computer in communication with the local instrument, thereby calibrating the local instrument.

2. The method of claim 1, further comprising the step of using the local instrument and the local calibration curve to quantify any of the analyte polynucleotide that may be present in a test sample.

3. The method of claim 1, wherein at least one of the first and second calibration curves was created using results obtained with the local instrument.

4. The method of claim 1, wherein both the first and second calibration curves were created using results obtained with the local instrument.

5. The method of claim 1, wherein neither the first calibration curve nor the second calibration curve was created using results obtained with the local instrument.

6. The method of claim 5, wherein a tangible form of the coefficients in step (a), and the adjustment calibrator of step (b) are both obtained in packaged combination with each other as a kit.

7. The method of claim 6, wherein the tangible form comprises a barcode.

8. The method of claim 1, wherein after step (c) and before step (d) there is the step of determining coordinates of a point where the first calibration curve and the second calibration curve intersect, the point being a pivot point common to each of the first, second, and local calibration curves.

9. The method of claim 8, wherein before step (a) there is a step for obtaining, in a machine-readable format, coefficients of a fitted equation for at least one of the first and second calibration curves.

10. The method of claim 8, further comprising the step of using the local instrument and the local calibration curve to quantify any of the analyte polynucleotide that may be present in a test sample.

11. The method of claim 1, wherein the first and second calibration curves are both linear calibration curves.

12. The method of claim 1, wherein the first and second calibration curves are both non-linear calibration curves.

13. The method of claim 1, wherein step (d) comprises comparing the result of step (c) with each of the first and second calibration curves, and further comprises calculating coordinates for a point on the local calibration curve.

14. The method of claim 13, wherein before step (a) there is a step for obtaining, in a machine-readable format, coefficients of a fitted equation for at least one of the first and second calibration curves.

15. The method of claim 13, further comprising the step of using the local instrument and the local calibration curve to quantify any of the analyte polynucleotide that may be present in a test sample.

16. The method of claim 1, further comprising the step of re-calibrating the local instrument using only a single adjustment calibrator.

17. The method of claim 1, wherein the real-time amplification reaction performed with the local instrument in step (c) is an isothermal nucleic acid amplification reaction.

18. The method of claim 1, wherein the real-time amplification reaction in step (c) comprises a transcription-associated amplification reaction.

19. The method of claim 1, wherein the analyte polynucleotide comprises RNA.

20. The method of claim 1, wherein before step (a) there is a step for obtaining, in a machine-readable format, coefficients of a fitted equation for at least one of the first and second calibration curves.

* * * * *